United States Patent
Blanchard et al.

(10) Patent No.: US 11,612,666 B2
(45) Date of Patent: Mar. 28, 2023

(54) PROCESS FOR THE PREPARATION OF DRUG LINKER COMPOUNDS

(71) Applicant: Seagen Inc., Bothell, WA (US)

(72) Inventors: Sophie Blanchard, Lake Forest Park, WA (US); James Coats, Edmonds, WA (US)

(73) Assignee: Seagen Inc., Bothell, WA (US)

( * ) Notice: Subject to any disclaimer, the term of this patent is extended or adjusted under 35 U.S.C. 154(b) by 296 days.

(21) Appl. No.: 16/768,027

(22) PCT Filed: Nov. 29, 2018

(86) PCT No.: PCT/US2018/063070
§ 371 (c)(1),
(2) Date: May 28, 2020

(87) PCT Pub. No.: WO2019/108797
PCT Pub. Date: Jun. 6, 2019

(65) Prior Publication Data
US 2020/0360532 A1    Nov. 19, 2020

Related U.S. Application Data

(60) Provisional application No. 62/593,104, filed on Nov. 30, 2017.

(51) Int. Cl.
| | | |
|---|---|---|
| *A61K 47/65* | (2017.01) | |
| *C07D 403/12* | (2006.01) | |
| *C07D 471/04* | (2006.01) | |
| *C07K 1/10* | (2006.01) | |
| *C07K 5/02* | (2006.01) | |
| *C07K 7/02* | (2006.01) | |
| *A61K 47/68* | (2017.01) | |
| *C07K 5/062* | (2006.01) | |

(52) U.S. Cl.
CPC ........ *A61K 47/6889* (2017.08); *C07D 403/12* (2013.01); *C07D 471/04* (2013.01); *C07K 5/02* (2013.01); *C07K 5/06052* (2013.01); *C07K 7/02* (2013.01)

(58) Field of Classification Search
CPC ............... A61K 47/6889; A61K 47/65; C07D 403/12; C07D 471/04; C07K 1/10; C07K 5/02; C07K 5/06052; C07K 7/02
See application file for complete search history.

(56) References Cited

U.S. PATENT DOCUMENTS

| | | |
|---|---|---|
| 6,214,345 B1 | 4/2001 | Firestone |
| 8,129,505 B2 | 3/2012 | Norman et al. |
| 2012/0003247 A1 | 1/2012 | Doronina |
| 2015/0105539 A1 | 4/2015 | Miao et al. |

FOREIGN PATENT DOCUMENTS

| | | | |
|---|---|---|---|
| CA | 2662981 A1 | 3/2008 | |
| JP | 2010530428 A | 9/2010 | |
| JP | 2014516050 A | 7/2014 | |
| JP | 2016501244 A | 1/2016 | |
| WO | 2008034124 A2 | 3/2008 | |
| WO | 2008034124 A3 | 8/2008 | |
| WO | WO-2014191578 A1 * | 12/2014 | ............. A61K 47/68 |
| WO | 2016046754 A1 | 3/2016 | |

OTHER PUBLICATIONS

Doronina, S.O. et al. (Jul. 2003). "Development of Potent Monoclonal Antibody Auristatin Conjugates for Cancer Therapy," Nat. Biotechnol. 21(7):778-784.

Dubowchik, G.M. et al. (2002). "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity," Chem. 13(4):855-869.

Extended European Search Report, dated Jul. 29, 2021, for European Patent Application No. 18883925.2, 14 pages.

Han, S.-Y. et al. (2004). "Recent Development Of Peptide Coupling Agents In Organic Synthesis," Tet. 60:2447-2476.

International Preliminary Report Report on Patentability, dated Jun. 2, 2020, for PCT/US2018/063070, filed Nov. 29, 2018, 6 pages.

International Search Report and Written Opinion of International Searching Authority, dated Feb. 11, 2019, for PCT/US2018/063070, filed Nov. 29, 2018, 19 pages.

International Union of Pure and Applied Chemistry (Nov. 5, 1960). "Definitive Rules for Nomenclature of Organic Chemistry," J. Am. Chem. Soc. 82:5545-5473, 30 pages.

Kolodych, S. et al. (2017, e-pub. Aug. 4, 2017). "Development and Evaluation of β-Galactosidase-Sensitive Antibody-Drug conjugates," European Journal of Medicinal Chemistry 142:376-382.

Levengood, M.R. et al. (Dec. 14, 2016). "Orthogonal Cysteine Protection Enables Homogeneous Multi-Drug Antibody-Drug Conjugates," Angew. Chem. 129:751-755.

Lu, J. et al. (Apr. 14, 2016). "Linkers Having a Crucial Role in Antibody-Drug Conjugates," Int. J. Mol. Sci. 17(14):561, 22 pages.

Pettit, G.R. et al. (Sep. 12, 2017). "Antineopiastic Agents. 604. The Path of Quinstatin Derivatives to Antibody Drug Conjgates," Journal of Natural Products 80(9):2447-2452.

* cited by examiner

*Primary Examiner* — Brenda L Coleman
(74) *Attorney, Agent, or Firm* — Morrison & Foerster LLP

(57) ABSTRACT

This disclosure generally relates to novel processes for the preparation of drug linker compounds and compositions comprising such drug linker compounds. The presently disclosed methods for synthesizing Fmoc-Val-Cit-PABOH and related compounds have also been found to minimize formation of diastereomeric impurities.

35 Claims, 1 Drawing Sheet

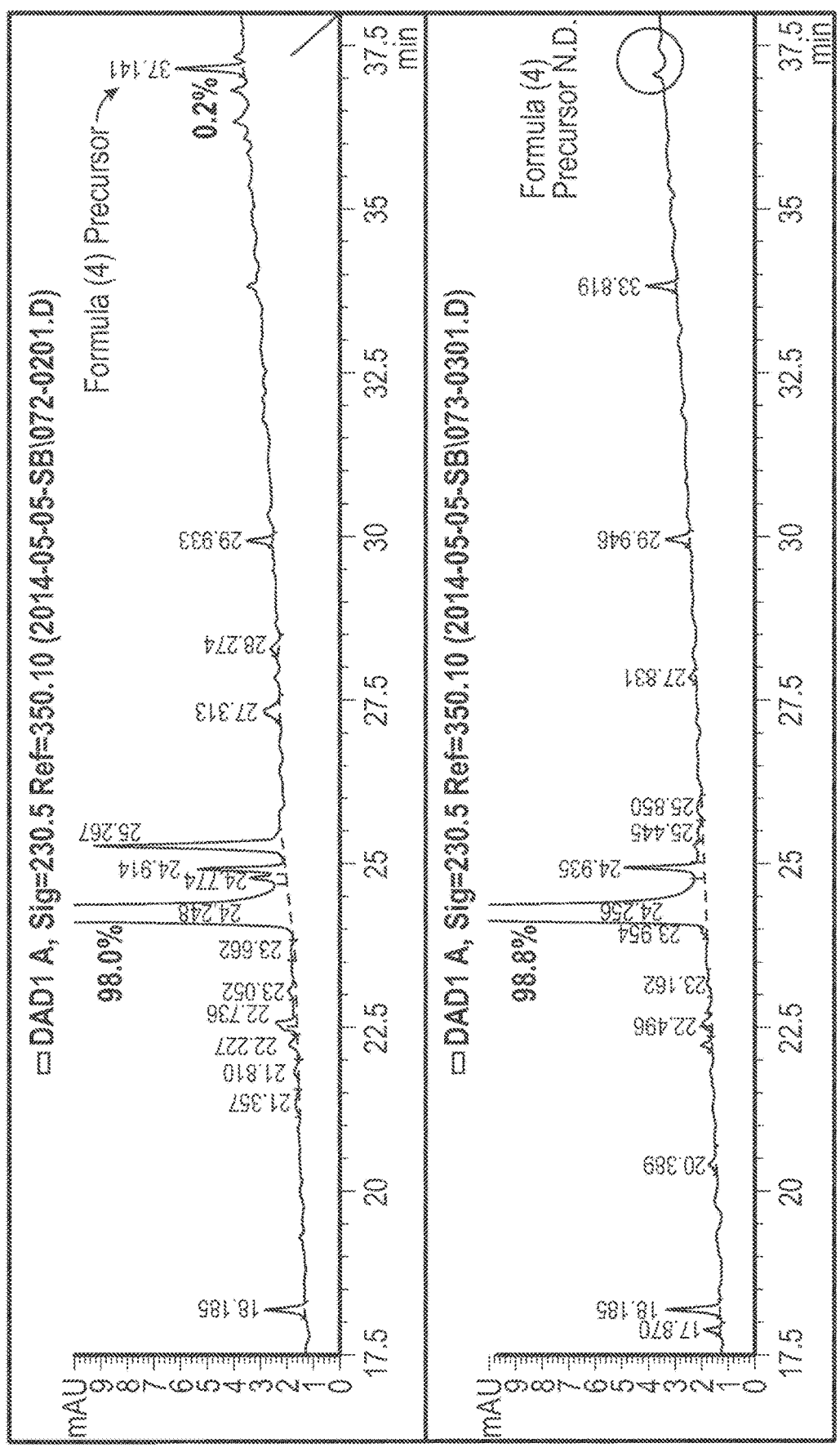

PROCESS FOR THE PREPARATION OF DRUG LINKER COMPOUNDS

CROSS-REFERENCE TO RELATED APPLICATION

This application is a national stage application under 35 U.S.C. § 371 of International Application No. PCT/US2018/063070, filed internationally on Nov. 29, 2018, which claims priority to U.S. Provisional application No. 62/593,104 filed on Nov. 30, 2017, the contents of which are incorporated herein by reference in their entirety.

FIELD

This disclosure generally relates to novel processes for the preparation of drug linker compounds and compositions comprising such drug linker compounds.

BACKGROUND

A great deal of interest has surrounded the use of monoclonal antibodies (mAbs) for the targeted delivery of cytotoxic agents to cancer cells. The design of antibody-drug conjugates typically involves attaching a cytotoxic agent to an antibody via a linker.

While a number of different linker compounds have been manufactured, commercially manufactured linker compounds often have various impurities that are difficult to remove.

Therefore, there is a need for improved methods for preparing such linker compounds with reduced amounts of contaminating impurities.

BRIEF SUMMARY

In one aspect, provided herein is a method of preparing a compound of Formula (1A):

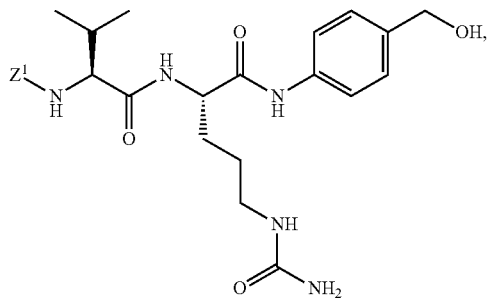

(1A)

or a salt thereof,
wherein $Z^1$ is a protecting group;
the method comprising reacting a compound of Formula (1B) or a salt thereof:

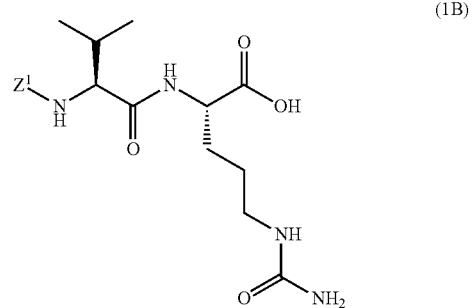

(1B)

with p-aminobenzyl alcohol (PABOH) in the presence of a peptide coupling reagent, wherein the peptide coupling reagent comprises

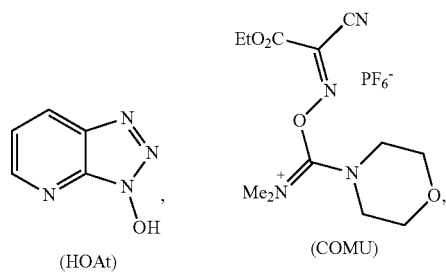

(HOAt)        (COMU)

or an HOAt derivative.

In some embodiments, the method further comprises converting the compound of Formula (1A) or a salt thereof to a compound of Formula (1D) or a salt thereof:

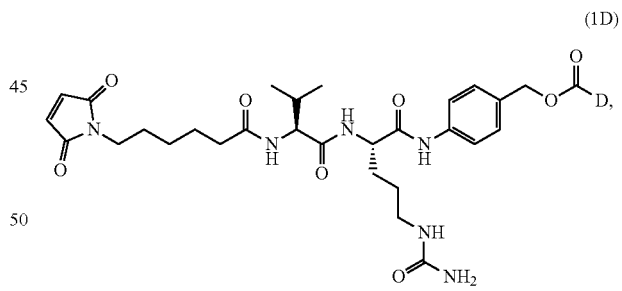

(1D)

wherein D is a moiety of Formula (D):

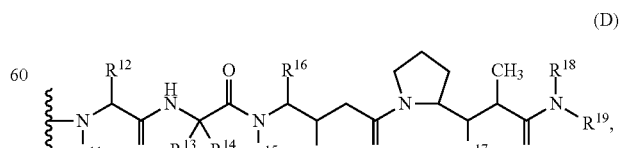

(D)

and $R^{11}$, $R^{12}$, $R^{13}$, $R^{14}$, $R^{15}$, $R^{16}$, $R^{17}$, $R^{18}$, and $R^{19}$ are as defined herein.

In some embodiments, the method further comprises converting the compound of Formula (1D) or a salt thereof to a compound of Formula (5):
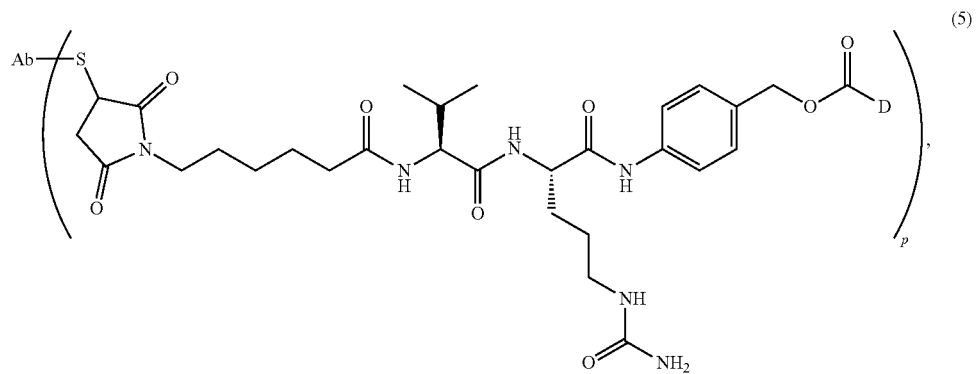
or a pharmaceutically acceptable salt thereof, wherein Ab and p are as defined herein.
In another aspect, provided herein is a compound of Formula (4):
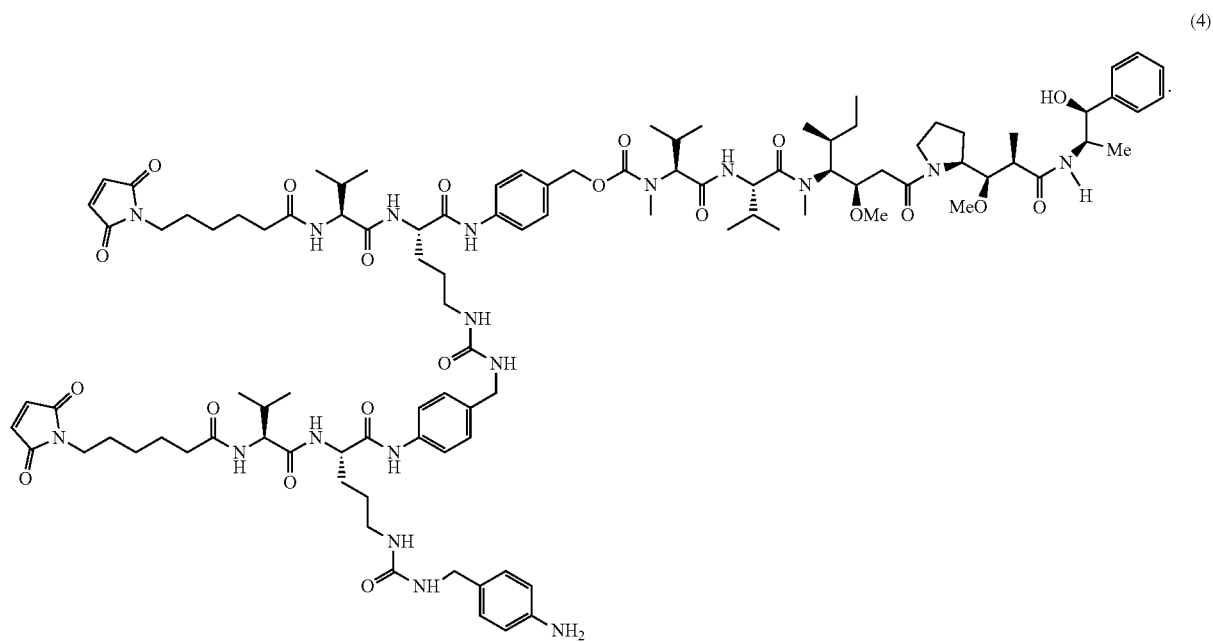 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(=O)NCc2ccc(NC(=O)[C@H](CCCNC(=O)NCc3ccc(N)cc3)NC(=O)[C@@H](NC(=O)CCCCCN3C(=O)C=CC3=O)C(C)C)cc2)NC(=O)[C@@H](NC(=O)CCCCCN2C(=O)C=CC2=O)C(C)C)cc1)C(C)C]

In another aspect, provided herein is a composition comprising a compound of Formula (3):

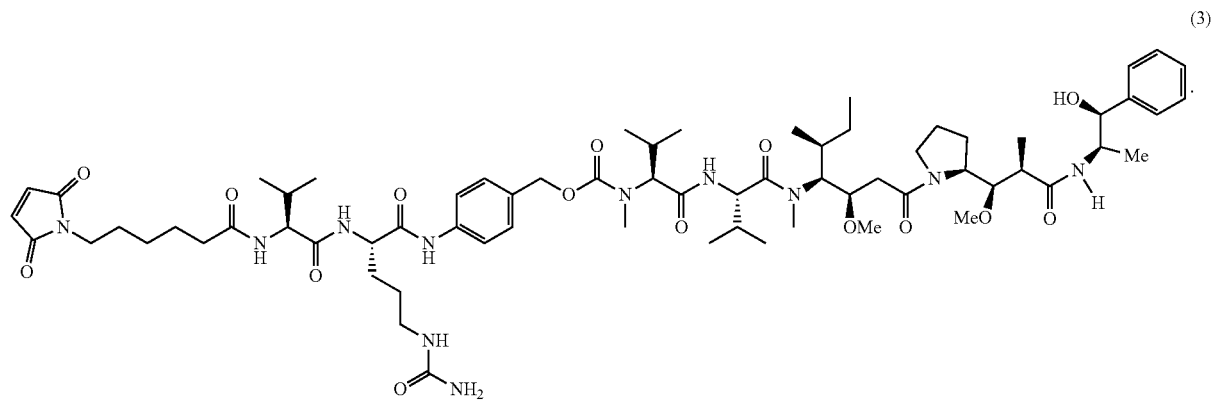 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

(3)

wherein the composition is substantially free of the compound of Formula (4).

In another aspect, provided herein is a composition comprising a compound of Formula (5), wherein the composition is substantially free of the compound of Formula (4) and any adducts of the compound of Formula (4) with an antibody.

FIGURE

The figure shows the results of analytical HPLC of Fmoc-Val-Cit-PABOH synthesized using a method similar to what that described in Dubowchik et al. (*Bioconjugate Chem.* 2002, 13, 855-869) (top) and the method of Example 3 described herein (bottom).

DETAILED DESCRIPTION

The compound of Formula (3):

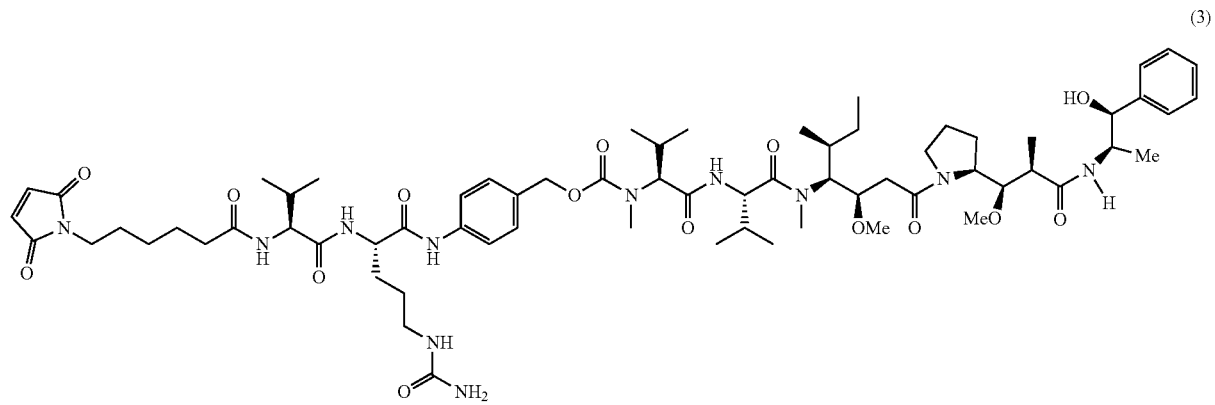 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

(3)

is a important starting material for manufacture of certain antibody-drug conjugates. However, known methods for synthesizinig the compound of Formula (3) have been shown to result in the formation of impurities that are difficult to remove. One such impurity that has been observed upon synthesis of the compound of Formula (3) is the compound of Formula (4):

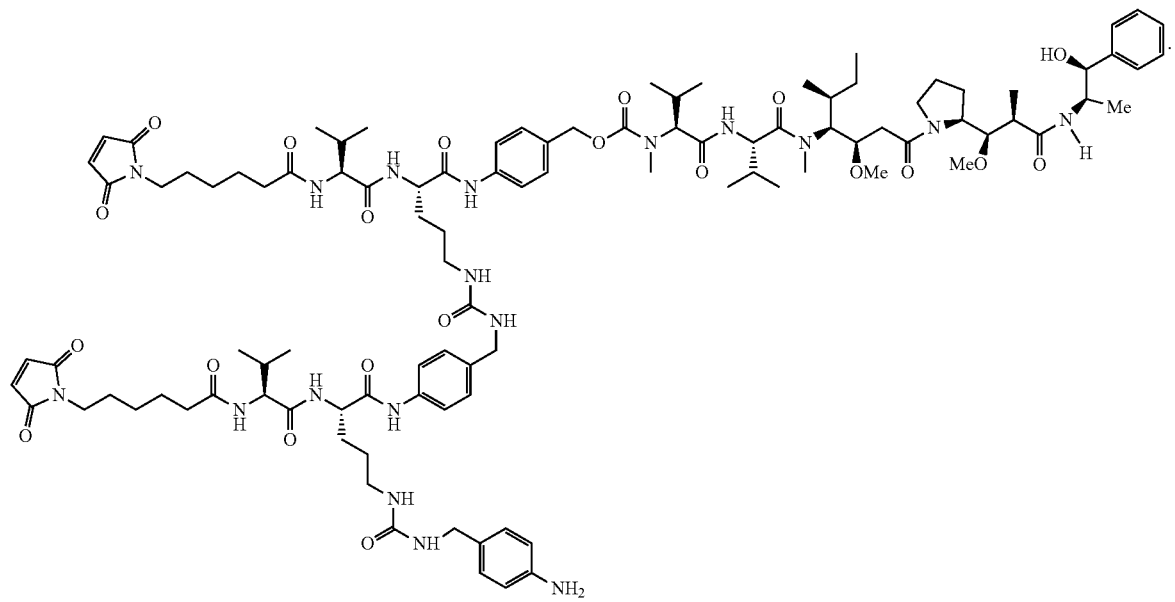

(4)

Impurities such as the compound of Formula (4) contribute to the formation of high molecular weight impurities in the bulk drug substance of antibody-drug conjugates prepared from Formula (3).

The compound of Formula (4) can result from a precursur compound formed during the synthesis of Fmoc-Val-Cit-PABOH, which is an upstream product in the synthesis of Formula (3).

precursor to Formula (4)

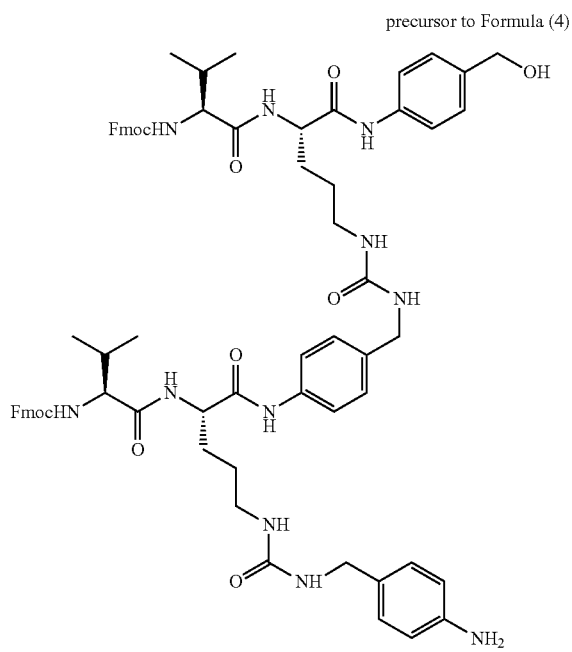

The present inventors have developed improved methods of synthesizing Fmoc-Val-Cit-PABOH and related compounds, which methods minimize or eliminate the formation of the precursor to Formula (4), and thereby minimize or eliminate the presence of Formula (4) in the downstream Formula (3) product. The improved methods also results in minimization or elimination of Formula (4) and other high molecular weight impurities, such as adducts of Formula (4) with an antibody, in antibody-drug conjugates prepared from Formula (3). The presently disclosed methods for synthesizing Fmoc-Val-Cit-PABOH and related compounds have also been found to minimize formation of diastereomeric impurities.

Definitions

As used herein and unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as used in the specification and the appended claims, the singular forms "a," "an," and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Embodiments also specifically include those compounds, compositions, compositions or methods that are, or that consist of, or that consist essentially of those specified components, elements or steps. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, the term "consisting essentially of" admits for the inclusion of unrecited elements that have no material effect on the functionality of the disclosed compositions, devices, articles of manufacture or methods for its intended purpose as further defined herein. The section headings used herein are for organizational purposes only and are not to be construed as limiting the subject matter described.

"About" as used herein when used in connection with a numeric value or range of values provided to describe a particular property of a compound or composition indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicates that the numeric value or range of values can vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, or 0.01% of the recited value or range of values, such as by 10% to 0.5% or by 5% to 1%, while still describing the particular property.

"Substantially" as the term is used herein means completely or almost completely; for example, a composition that is "substantially free" of a component either has none of the component or contains no more than about 1% by weight of the compound, about 0.5% by weight of the compound, about 0.1% by weight of the compound, about 0.05% by weight of the compound, about 0.01% by weight of the compound, about 0.005% by weight of the compound, about 0.001% by weight of the compound, about 0.0005% by weight of the compound, or about 0.0001% by weight of the compound.

"Moiety" as used herein means a specified segment, fragment, or functional group of a molecule or compound. Chemical moieties are sometimes indicated as chemical entities that are embedded in or appended to (i.e., a substituent or variable group) a molecule, compound or chemical Formula.

Unless indicated otherwise, for any substituent group or moiety described herein by a given range of carbon atoms, the designated range means that any individual number of carbon atoms is described. Thus, reference to, e.g., "optionally substituted $C_1$-$C_4$ alkyl" or "optionally substituted $C_2$-$C_6$ alkenyl" specifically means that a 1, 2, 3, or 4 carbon alkyl moiety, optionally substituted, as defined herein, is present, or a 2, 3, 4, 5, or 6 carbon alkenyl moiety, optionally substituted, as defined herein, is present, respectively. All such numerical designations are expressly intended to disclose all of the individual carbon atom groups; and thus "optionally substituted $C_1$-$C_4$ alkyl" includes, methyl, ethyl, 3-carbon alkyls, and 4-carbon alkyls, including all of their positional isomers, whether substituted or unsubstituted. Thus, when an alkyl moiety is substituted, the numerical designations refer to an unsubstituted base moiety and are not intended to include carbon atoms that may be present in the substituents of that base moiety.

The organic substituents, moieties, and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as used herein, by itself or as part of another term, unless otherwise stated or implied by context, refers to a saturated, linear or branched, non-cyclic hydrocarbon radical, wherein the hydrocarbon radical is methyl or has the indicated number of covalently linked saturated carbon atoms, e.g., "$C_1$-$C_6$ alkyl" or "C1-C6 alkyl" means a saturated alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to a saturated alkyl moiety or group having 1 saturated carbon atom or 2, 3, 4, 5, 6, 7 or 8 contiguous saturated, non-cyclic carbon atoms. The number of saturated carbon atoms in an alkyl moiety or group can vary and may be 1 to 50, 1 to 30 or 1 to 20, or 1 to 12, (e.g., 1 to 8, 1 to 6 or 1 to 4). In some aspects, alkyl refers to a saturated $C_1$-$C_{12}$ or a $C_1$-$C_8$ alkyl moiety, such as a saturated $C_1$-$C_6$ or $C_1$-$C_4$ alkyl moiety, with the latter sometimes referred to as lower alkyl. When the number of carbon atoms is not indicated, an alkyl moiety, group or substituent has from 1 to 8 saturated carbon atoms. Unless otherwise stated or implied by context, an alkyl moeity, group or substituent is optionally substituted. When an alkyl substituent is unsaturated such moieties may be unsaturated $C_3$-$C_{12}$ alkyl or $C_3$-$C_8$ moieties, such as unsaturated $C_1$-$C_6$ alkyl moieties.

Exemplary alkyl groups include, without limitation, methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, and sec-amyl and in other aspects an alkyl substituent, moiety or group are or are additionally exemplified by other linear and branch chain alkyl moieties.

"Carbocyclyl" as used herein, by itself of as part of another term, unless otherwise stated or implied by context, refers to a radical of a monocyclic, bicyclic, or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more sp$^3$ carbons). Thus, a carbocyclyl is a cyclic arrangement of saturated carbons but may also contain unsaturated carbon atom(s) and therefore its carbocyclic ring may be saturated or partially unsaturated or may be fused with an aromatic ring system, wherein the points of fusion to the carbocyclic and aromatic ring systems are to adjacent carbons of each of these ring systems.

When carbocyclyl is used as a substituent the carbocyclyl is attached to another organic moiety with which it is associated through a carbon atom that is involved in the carbocyclic ring system of the carbocyclyl moiety provided that carbon atom is not aromatic. The number of carbon atoms in a carbocyclyl moeity group or substituent is defined by the total number of skeletal atoms of its carbocyclic ring system. That number can vary and in some embodiments ranges from 3 to 50, 3 to 30, 3 to 20 or 3 to 12, such as from 3 to 8 or 3 to 6 skeletal carbon atoms unless otherwise specified, e.g., $C_3$-$C_8$ carbocyclyl means an carbocyclyl substituent, moiety or group containing 3, 4, 5, 6, 7, or 8 carbocyclic carbon atoms and $C_3$-$C_6$ carbocyclyl means a carbocyclyl substituent, moiety or group containing 3, 4, 5, or 6 carbocyclic carbon atoms. Exemplary $C_3$-$C_8$ carbocyclyls include, without limitation, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Therefore, carbocyclyl substituents, moieties or groups in some embodiments have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share one (i.e., is a spiro ring system) or two carbon atoms and a tricyclic ring system may share a total of 2, 3, or 4 carbon atoms, such as 2 or 3. Unless otherwise stated or implied by context, a carbocyclyl is optionally substituted. In other aspects, a $C_3$-$C_8$ cycloalkyl moiety, group or substituent is selected from the group consisting of cyclopropyl, cyclopentyl and cyclohexyl, or is encompassed or further encompassed by other cyclic moieties that have no more than 8 carbon atoms in their cyclic ring systems. When the number of carbon atoms is not indicated, a carbocyclyl moiety, group or substituent has from 3 to 8 carbon atoms in its carboxcylic ring system.

"Alkenyl" as used herein, by itself or as part of another term, unless otherwise stated or implied by context, refers to an organic moiety, substituent or group that comprises one or more double bond functional groups (e.g., a —CH=CH— moiety) or 1, 2, 3, 4, 5, or 6 or more, such as 1, 2, or 3 of such functional groups, and in some embodiments one such functional group, and in some aspects may be substituted (i.e., is optionally substituted) with an aryl moiety, or linked normal, secondary, tertiary or cyclic carbon atoms, i.e., linear, branched, or any combination thereof unless the alkenyl substituent, moiety or group is a vinyl moiety (e.g., a —CH=CH$_2$ moiety). An alkenyl moiety, group or substituent having multiple double bonds may have the double bonds arranged contiguously (i.e., a 1,3-butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

"Alkynyl" as used herein, by itself or as part of another term, unless otherwise stated or implied by context, refers to an organic moiety, substituent or group that comprises one or more triple bond functional groups (e.g., a —C≡C— moiety) or 1, 2, 3, 4, 5, or 6 or more, such as 1, 2, or 3 of such functional groups, and in some embodiments one such functional group, and in some aspects may be substituted (i.e., is optionally substituted) with an aryl moiety such as phenyl, or by an alkenyl moiety or linked normal, secondary, tertiary or cyclic carbon atoms, i.e., linear, branched, cyclic or any combination thereof. An alkynyl moiety, group or substituent having multiple triple bonds may have the triple bonds arranged contiguously or non-contiguously with one or more intervening saturated or unsaturated carbon atoms or a combination thereof, provided that a cyclic, contiguous arrangement of triple bonds do not form a cyclic conjugated system of 4n+2 electrons (i.e., is not aromatic).

"Aryl" as used herein, by itself or as part of another term, unless otherwise stated or implied by context, refers to an organic moiety, substituent or group having an aromatic or fused aromatic ring system with no ring heteroatoms comprising 1, 2, 3, or 4 to 6 aromatic rings, such as 1 to 3 aromatic rings or 1 or 2 aromatic rings, wherein the rings are composed of only carbon atoms that participate in a cyclically conjugated system of 4n+2 electrons (Hückel rule), such as 6, 10, or 14 electrons, some of which may additionally participate in exocyclic conjugation with a heteroatom (cross-conjugated, e.g., quinone). Aryl substituents, moieties or groups may be formed by six, eight, ten, or more aromatic carbon atoms up to 24 to include $C_6$-$C_{24}$ aryl. Unless otherwise stated or implied by context, aryl substituents, moieties or groups are optionally substituted. Exemplary aryls are $C_6$-$C_{10}$ aryls such as phenyl and naphthalenyl and phenanthryl. As aromaticity in a neutral aryl moiety requires an even number or electrons, it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group.

"Arylalkyl" or "heteroarylalkyl" as the terms are used herein, by itself or as part of another term, refers to an aryl or heteroaryl moiety bonded to an alkyl moiety, i.e., (aryl)-alkyl-, where alkyl and aryl groups are as described above. In some embodiments an arylalkyl is a ($C_6$-$C_{24}$ aryl)-$C_1$-$C_{12}$ alkyl moiety, group or substituent, and heteroarylalkyl is a ($C_5$-$C_{24}$ heteroaryl)-$C_1$-$C_{12}$ alkyl moiety, group or substituent. When (hetero)arylalkyl is used as a substituent the alkyl moiety of the (hetero)arylalkyl is attached to another organic moiety with which it is associated through a sp$^3$ carbon of its alkyl moiety. In some aspects an arylalkyl is a ($C_6$-$C_{10}$ aryl)-$C_1$-$C_{12}$ alkyl, such as a ($C_6$-$C_{10}$ aryl)-$C_1$-$C_6$ exemplified without limitation, by $C_6H_5$—$CH_2$—, $C_6H_5$—$CH(CH_3)$CH$_2$— and $C_6H_5$—$CH_2$—$CH(CH_2CH_2CH_3)$—.

"Alkylaryl" or "alkylheteroaryl," as used herein, by itself or as part of another term, unless otherwise stated or implied by context, refers to an alkyl moiety bonded to an aryl or heteroaryl moiety, i.e., -(hetero)aryl-alkyl, where (hetero)aryl and alkyl groups are as described above. In some embodiments, an alkylaryl is a ($C_1$-$C_{12}$ alkyl)-$C_6$-$C_{24}$ aryl-moiety, group or substituent, and alkylheteroaryl is a ($C_1$-$C_{12}$ alkyl)-$C_5$-$C_{24}$ heteroaryl-moiety, group or substituent. When alkyl(hetero)aryl is used as a substituent the (hetero)aryl moiety of the alkyl(hetero)aryl is attached to another organic moiety with which it is associated through an aromatic carbon atom or heteroatom of its aryl or heteroaryl moiety. In some aspects, an alkylaryl is a ($C_1$-$C_{12}$ alkyl)-$C_6$-$C_{10}$ aryl- or a ($C_1$-$C_6$ alkyl)-$C_6$-$C_{10}$ aryl-exemplified without limitation, for example, by —$C_6H_4$—$CH_3$ or —$C_6H_4$—$CH_2CH(CH_3)_2$.

"Heterocyclyl," as the term is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms, optionally substituted where permitted, including without limitation N/NH, O, S, Se, B, Si, and P, wherein two or more heteroatoms may be adjacent to each other or separated by one or more carbon atoms within the same ring system, such as by 1 to 3 atoms. In some embodiments, those heteroatoms are N/NH, O, and S. A heterocyclyl in some embodiments contains a total of one to ten heteroatoms in the heterocyclic ring system provided that not all of the skeletal atoms of any one ring in the heterocyclic ring system are heteroatoms, wherein each heteroatom in the ring(s), optionally substituted where permitted, is independently selected from the group consisting of N/NH, O, and S, with the proviso that any one ring does not contain two adjacent O or S atoms. Exemplary heterocyclyls and heteroaryls are collectively referred to as heterocycles, are provided by Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5545-5473 particularly 5566-5573).

When heterocyclyl is used as a substituent, a saturated or partially unsaturated heterocyclic ring of the heterocyclyl is attached to another organic moiety with which it is associated through a carbon atom or a heteroatom of that heterocyclic ring, where such attachment does not result in an unstable or disallowed formal oxidation state of that carbon or heteroatom. A heterocyclyl in that context is a monovalent moiety in which a heterocyclic ring of the heterocyclic ring system defining it as a heterocyclyl is non-aromatic, but may be fused with a carbocyclic, aryl or heteroaryl ring and includes phenyl- (i.e., benzo) fused heterocyclic moieties.

In some embodiments, a heterocyclyl is a $C_3$-$C_{20}$ carbocyclyl wherein 1, 2 or 3 carbons of its cycloalkyl ring system is replaced along with its attached hydrogens with a heteroatom selected from the group consisting of optionally substituted N/NH, O, and S and thus is a $C_3$-$C_{20}$ heterocyclyl, such as a $C_3$-$C_{12}$ heterocyclyl, or a $C_5$-$C_{12}$, $C_3$-$C_6$, or $C_5$-$C_6$ heterocyclyl in which the subscript indicates the total number of skeletal atoms (inclusive of its carbon atoms and heteroatoms) of the heterocyclic ring system of the heterocyclyl. In some aspects a heterocyclyl contains 0 to 2 N atoms, 0 to 2 O atoms, or 0 to 1 S atoms or some combination thereof provided at least one of said heteroatoms is present in the cyclic ring system, which may be substituted at a carbon atom with an oxo (═O) moiety, as in pyrrolidin-2-one, or at a heteroatom with one or two oxo moieties so as to contain an oxidized heteroatom as exemplified, but not limited to, —N(═O), —S(═O)—, or —S(═O)$_2$—. In some embodiments, heterocyclyl is selected from the group consisting of pyrrolidinyl, piperidinyl, morpholinyl and piperazinyl.

"Heteroaryl" as the term is used herein, by itself or as part of another term, unless otherwise stated or implied by context, refers to an aryl moiety, group or substituent as defined herein in which one or more but not all of the aromatic carbons of an aromatic ring system of the aryl is replaced by a heteroatom. A heteroaryl in some embodiments contains a total one to four heteroatoms in the ring(s) of the heteroaryl ring system, provided that not all of the skeletal atoms of any one ring system in the heteroaryl are heteroatoms, optionally substituted where permitted, and have 0 to 3 N atoms, 1 to 3 N atoms, or 0 to 3 N atoms, such as 0 to 1 O atoms and/or 0 to 1 S atoms, provided that at least one heteroatom is present. A heteroaryl may be monocyclic, bicyclic or polycyclic. A monocyclic heteroaryl in some embodiments is a $C_5$-$C_{24}$ heteroaryl, such as a $C_5$-$C_{12}$ or $C_5$-$C_6$ heteroaryl, in which the subscript indicates the total number of skeletal atoms (inclusive of its carbon atoms and heteroatoms) of the aromatic ring system(s) of the heteroaryl. In some aspects a heteroaryl is an aryl moiety wherein one 1, 2, or 3 of the carbon atoms of the aromatic ring(s) and their attached hydrogen atoms of a parent aryl moiety are replaced by a heteroatom, optionally substituted where permitted, including N/NH, O and S, provided that not all of the skeletal atoms of any one aromatic ring system in the aryl moiety are replaced by heteroatoms and in some embodiments are replaced by oxygen (—O—), sulfur (—S—) nitrogen (═N—) or —NR—, so that the nitrogen heteroatom is optionally substituted, wherein R is —H, a nitrogen protecting group or optionally substituted $C_1$-$C_{20}$ alkyl or is an optionally substituted $C_6$-$C_{24}$ aryl or $C_5$-$C_{24}$ heteroaryl to form a biaryl. In other aspects one 1, 2, or 3 of the carbon atoms of the aromatic ring(s) and their attached hydrogen atoms of a parent aryl moiety are replaced by nitrogen substituted with another organic moiety in a manner which retains the cyclic conjugated system. In aspects, the nitrogen, sulfur or oxygen heteroatom participates in the conjugated system either through pi-bonding with an adjacent atom in the ring system or through a lone pair of electrons on the heteroatom. In still other aspects, a heteroaryl has the structure of a heterocyclyl as defined herein in which its ring system has been aromatized.

In some embodiments, a heteroaryl is monocyclic, which in some aspects has a 5-membered or 6-membered heteroaromatic ring system. A 5-membered heteroaryl is a monocyclic $C_5$-heteroaryl containing 1 to 4 aromatic carbon atoms and the requisite number of aromatic heteroatoms within its heteroaromatic ring system. A 6-membered heteroaryl is a monocyclic $C_6$ heteroaryl containing 1 to 5 aromatic carbon atoms and the requisite number of aromatic heteroatoms within its heteroaromatic ring system. Heteroaryls that are 5-membered have four, three, two, or one aromatic heteroatom(s), and heteroaryls that are 6-membered include heteroaryls having five, four, three, two, or one aromatic heteroatom(s). Exemplary $C_5$-heteroaryls include, without limitation, pyrrolyl, furanyl, thiophenyl, oxazolyl, isoxazolyl, thiazolyl, isothiazolyl, imidazolyl, pyrazolyl, triazolyl and tetrazolyl. Exemplary $C_6$ heteroaryls include, without limitation, pyridinyl, pyridazinyl, pyrimidinyl, and triazinyl.

"Heteroalkyl," as used herein by itself or in combination with another term, unless otherwise stated or implied by context, refers to an optionally substituted straight or branched chain hydrocarbon, fully saturated or containing from 1 to 3 degrees of unsaturation and consisting of 1 to 12 carbon atom and 1 to 6 heteroatoms, such 1 to 5 heteroatoms or one or two heteroatoms, selected from the group consisting of O, N, Si and S, optionally substituted where permitted, and includes each nitrogen and sulfur atom independently optionally oxidized to an N-oxide, a sulfoxide or sulfone, or wherein one of the nitrogen atoms is optionally quaternized. The heteroatom(s) O, N, S, and/or Si may be placed at any interior position of the heteroalkyl group or at a terminal position of the optionally substituted alkyl group of the heteroalkyl. In some aspects, the heteroalkyl is fully saturated or contains 1 degree of unsaturation and consists of 1 to 6 carbon atoms and 1 to 2 heteroatoms, and in other aspects that heteroalkyl is unsubstituted. Non-limiting examples are —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —NH—CH$_2$—CH$_2$—NH—C(O)—CH$_2$—CH$_3$, —CH$_2$—CH$_2$—S(O)$_2$—CH$_3$, —CH═CH—O—CH$_3$, —Si(CH$_3$)$_3$, —CH$_2$—CH═N—O—CH$_3$, and —CH═CH—N(CH$_3$)—CH$_3$. Up to two heteroatoms may be consecutive, as exemplified by —CH$_2$—NH—OCH$_3$ and —CH$_2$—O—Si(CH$_3$)$_3$. A heteroalkyl is typically denoted by the number of its contiguous heteroatom(s) and non-aromatic carbon atoms of its alkyl moiety unless indicated otherwise or by context. Thus, —CH$_2$—CH$_2$—O—CH$_3$ and —CH$_2$—CH$_2$—S(O)—CH$_3$ are both $C_4$-heteroalkyls and —CH$_2$—CH═N—O—CH$_3$, and —CH═CH—N(CH$_3$)—CH$_3$ are both $C_5$ heteroalkyls.

"Optionally substituted alkyl", "optionally substituted alkenyl", "optionally substituted alkynyl", "optionally substituted alkylaryl", "optionally substituted arylalkyl", "optionally substituted heterocycle", "optionally substituted aryl", "optionally substituted heteroaryl", "optionally substituted alkylheteroaryl", "optionally substituted heteroarylalkyl" and like terms refer to an alkyl, alkenyl, alkynyl, alkylaryl, arylalkyl heterocycle, aryl, heteroaryl, alkylheteroaryl, heteroarylalkyl, or other substituent, moiety or group as defined or disclosed herein wherein hydrogen atom(s) of that substituent, moiety or group has been optionally replaced with different moiety(ies) or group(s), or wherein an alicyclic carbon chain that comprise one of those substituents, moiety or group is interrupted by replacing carbon atom(s) of that chain with different moiety(ies) or group(s). In some aspects an alkene functional group replaces two contiguous $sp^3$ carbon atoms of an alkyl substituent, provided that the radical carbon of the alkyl moiety is not replaced, so that the optionally substituted alkyl becomes an unsaturated alkyl substituent. It is understood that where the term "optionally substituted" is used herein, the disclosure includes embodiments in which the substituent, moiety or group is substituted and embodiments in which the substituent, moiety or group is unsubstituted.

An optional substituent replacing hydrogen(s) in any one of the foregoing substituents, moieties, or groups is independently selected from the group consisting of $C_6$-$C_{24}$ aryl, $C_5$-$C_{24}$ heteroaryl, hydroxyl, $C_1$-$C_{20}$ alkoxy, $C_6$-$C_{24}$ aryloxy, cyano, halogen, nitro, $C_1$-$C_{20}$ fluoroalkoxy, and amino, which encompasses —$NH_2$ and mono-, di-, and tri-substituted amino groups, and the protected derivatives thereof, or is selected from the group consisting of —X, —OR', —SR', —$NH_2$, —N(R')($R^{op}$), —N($R^{op}$)$_3$, =NR', —$CX_3$, —CN, —$NO_2$, —NR'C(=O)H, —NR'C(=O)$R^{op}$, —NR'C(=O)$R^{op}$, —C(=O)R', —C(=O)$NH_2$, —C(=O)N(R')$R^{op}$, —S(=O)$_2$$R^{op}$, —S(=O)$_2$$NH_2$, —S(=O)$_2$N(R')$R^{op}$, —S(=O)$_2$$NH_2$, —S(=O)$_2$N(R')$R^{op}$, —S(=O)$_2$OR', —S(=O)$R^{op}$, —OP(=O)(OR')(O$R^{op}$), —OP(OH)$_3$, —P(=O)(OR')(O$R^{op}$), —PO$_3$H$_2$, —C(=O)R', —C(=S)$R^{op}$, —CO$_2$R, —C(=S)O$R^{op}$, —C(=O)SR', —C(=S)SR', —C(=S)$NH_2$, —C(=S)N(R')($R^{op}$)$_2$, —C(=NR')$NH_2$, —C(=NR')N(R')$R^{op}$, and salts thereof, wherein each X is independently selected from the group consisting of halogens: —F, —Cl, —Br, and —I; and wherein each $R^{op}$ is independently selected from the group consisting of $C_1$-$C_{20}$ alkyl, $C_2$-$C_{20}$ alkenyl, $C_2$-$C_{20}$ alkynyl, $C_6$-$C_{24}$ aryl, $C_3$-$C_{24}$ heterocyclyl, $C_5$-$C_{24}$ heteroaryl, a protecting group, and a prodrug moiety or two of $R^{op}$ together with the heteroatom to which they are attached defines a $C_3$-$C_{24}$ heterocyclyl; and R' is hydrogen or $R^{op}$, wherein $R^{op}$ is selected from the group consisting of $C_1$-$C_{20}$ alkyl, $C_6$-$C_{24}$ aryl, $C_3$-$C_{24}$ heterocyclyl, $C_5$-$C_{24}$ heteroaryl, and a protecting group.

In some embodiments, optional substituents that are present are selected from the group consisting of —X, —OH, —O$R^{op}$, —SH, —S$R^{op}$, —$NH_2$, —NH($R^{op}$), —NR'($R^{op}$)$_2$, —N($R^{op}$)$_3$, —NH, =N$R^{op}$, —$CX_3$, —CN, —$NO_2$, —NR'C(=O)H, NR'C(=O)$R^{op}$, —CO$_2$H, —C(=O)H, —C(=O)$R^{op}$, —C(=O)$NH_2$, —C(=O)NR'$R^{op}$, —S(=O)$_2$$R^{op}$, —S(=O)$_2$$NH_2$, —S(=O)$_2$N(R')$R^{op}$, —S(=O)$_2$$NH_2$, —S(=O)$_2$N(R')($R^{op}$), —S(=O)$_2$OR', —S(=O)$R^{op}$, —C(=S)$R^{op}$, —C(=S)$NH_2$, —C(=S)N(R')$R^{op}$, —C(=NR')N($R^{op}$)$_2$, and salts thereof, wherein each X is independently selected from the group consisting of —F and —Cl, $R^{op}$ is in some embodiments selected from the group consisting of $C_1$-$C_6$ alkyl, $C_6$-$C_{10}$ aryl, $C_3$-$C_{10}$ heterocyclyl, $C_5$-$C_{10}$ heteroaryl, and a protecting group; and R' is independently selected from the group consisting of hydrogen, $C_1$-$C_6$ alkyl, $C_6$-$C_{10}$ aryl, $C_3$-$C_{10}$ heterocyclyl, $C_5$-$C_{10}$ heteroaryl, and a protecting group, independently selected from $R^{op}$.

In some embodiments, optional substituents that are present are selected from the group consisting of —X, —$R^{op}$, —OH, —O$R^{op}$, —$NH_2$, —NH($R^{op}$), —N($R^{op}$)$_2$, —N($R^{op}$)$_3$, —$CX_3$, —$NO_2$, —NHC(=O)H, —NHC(=O)$R^{op}$, —C(=O)$NH_2$, —C(=O)NH$R^{op}$, —C(=O)N($R^{op}$)$_2$, —CO$_2$H, —CO$_2$$R^{op}$, —C(=O)H, —C(=O)$R^{op}$, —C(=O)$NH_2$, —C(=O)NH($R^{op}$), —C(=O)N($R^{op}$)$_2$, —C(=NR')$NH_2$, —C(=NR')NH($R^{op}$), —C(=NR')N($R^{op}$)$_2$, a protecting group and salts thereof, wherein each X is —F; $R^{op}$ is independently selected from the group consisting of $C_1$-$C_6$ alkyl, $C_6$-$C_{10}$ aryl, $C_5$-$C_{10}$ heteroaryl and a protecting group; and R' is selected from the group consisting of hydrogen, $C_1$-$C_6$ alkyl and a protecting group, independently selected from $R^{op}$.

"Halogen" as used herein, unless otherwise stated or implied by context, refers to fluorine, chlorine, bromine, or iodine and is in some embodiments —F or —Cl.

"Alkoxy" as used herein, refers to an —O-alkyl group, where the O is the point of attachment to the rest of the molecule, and alkyl is as defined above.

"Aryloxy" as used herein, refers to an —O-aryl group, where the O is the point of attachment to the rest of the molecule, and aryl is as defined above.

"Protecting group" as used herein, unless otherwise stated or implied by context, refers to a moiety that prevents or substantially reduces the ability of the atom or functional group to which it is linked from participating in unwanted reactions. Typical protecting groups for atoms or functional groups are given in Greene (2014), "Protective groups in organic synthesis, $5^{th}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —O$R^{PR}$, wherein $R^{PR}$ is a protecting group for hydroxyl, wherein hydroxyl is in some embodiments protected as an ester (e.g., acetate, propionate or benzoate). Other protecting groups for hydroxyl avoid its interference with the nucleophilicity of organometallic reagents or other highly basic reagents, for which purpose hydroxyl is in some embodiments protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NH$R^{PR}$ or —N($R^{PR}$)$_2$, wherein least one of $R^{PR}$ is a nitrogen atom protecting group or both $R^{PR}$ together define a nitrogen atom protecting group.

A protecting group is a suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. In other aspects, a suitable protecting group is a protecting group used in peptide coupling reactions. For example, a suitable protecting group for the basic nitrogen atom of an acyclic or cyclic basic group is an acid-labile carbamate protecting group such as t-butyloxycarbonyl (BOC).

A "carboxyl-activating" group or procedure, as the term is used herein, refers to a group replacing the hydroxyl group of a carboxyl to form a species that more readily undergoes reactions with nucleophilic reagents such as alcohols and amines. An example is an acyl halide, such as an acid chloride, that is activated for reactions leading to the formation of esters and amides. Another example is an N-hydroxy ester of a carboxylic acid, such as an N-hydroxysuccinimide ester, or an N-hydroxybenzotriazole ester. Another example is a carbodiimide that reacts with the hydroxyl group of a carboxyl group to form an O-acylisourea, that is thus activated for subsequent reaction with a nucleophile.

"Pharmaceutically acceptable salt" as used herein, refers to pharmaceutically acceptable organic or inorganic salts of a compound. The compound may contain at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterions.

In some embodiments, a pharmaceutically acceptable salt is selected from those described in P. H. Stahl and C. G. Wermuth, editors, *Handbook of Pharmaceutical Salts: Properties, Selection and Use*, Weinheim/Zürich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

"Antibody" as used herein is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment have the requisite number of attachment sites for a drug-linker. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system (see, e.g., Janeway et al., 2001, *Immunol. Biology*, 5th Ed., Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some embodiments, the antibody is of human or murine origin.

In some aspects an antibody selectively and specifically binds to an epitope on hyper-proliferating cells or hyper-stimulated mammalian cells (i.e., abnormal cells), wherein the epitope is preferentially displayed by or is more characteristic of the abnormal cells in contrast to normal cells, or is preferentially displayed by or is more characteristic of normal cells in the vicinity of abnormal cells in contrast to normal cells not localized to the abnormal cells. In those aspects the mammalian cells are may be human cells.

"Monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

"Antigen" is an entity that is capable of selective binding to an unconjugated antibody or a fragment thereof or to an antibody-drug conjugate comprising an antibody Ligand Unit corresponding to or incorporating that antibody or fragment thereof. In some aspects, the antigen is an extracellularly-accessible cell-surface protein, glycoprotein, or carbohydrate preferentially displayed by abnormal or other unwanted cells in comparison to normal cells. In some instances the unwanted cells having the antigen are hyper-proliferating cells in a mammal. In other instances, the unwanted cells having the antigen are hyper-activated immune cells in a mammal. In other aspects, the specifically bound antigen is present in the particular environment of hyper-proliferating cells or hyper-activated immune cells in a mammal in contrast to the environment typically experienced by normal cells in the absence of such abnormal cells. In still other aspects the cell-surface antigen is capable of internalization upon selective binding of an antibody-drug conjugate compound and is associated with cells that are particular to the environment in which hyper-proliferating or hyper-stimulated immune cells are found in the absence of such abnormal cells. An antigen is an exemplary targeted moiety of an antibody-drug conjugate, wherein its targeting antibody Ligand Unit corresponds to or incorporates an antibody to a targeted antigen and is capable of preferentially recognizing that antigen through selective binding.

Antigens associated with cancer cells that are cell-surface accessible to an antibody-drug conjugate include by way of example and not limitation CD19, CD70, CD30, CD33, CD48, NTB-A, $\alpha v \beta 6$, and CD123.

The term "therapeutically effective amount" refers to an amount of a drug effective or an antibody conjugate of the drug to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

Methods

In some embodiments, provided herein is a method of preparing a compound of Formula (1A'):

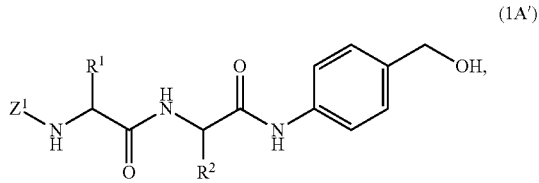

(1A')

or a salt thereof,
wherein $Z^1$ is a protecting group; and
$R^1$ and $R^2$ are each independently a side chain of an α-amino acid, the method including reacting a compound of Formula (1B') or a salt thereof:

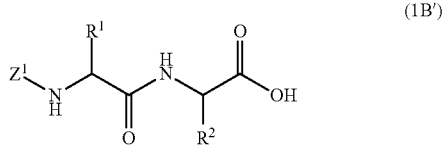

(1B')

with p-aminobenzyl alcohol (PABOH) in the presence of a peptide coupling reagent, wherein the peptide coupling reagent comprises

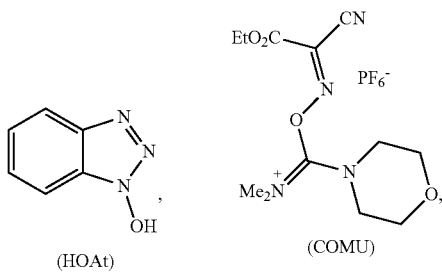

(HOAt) (COMU)

or an HOAt derivative.

As used herein, an "α-amino acid" is a compound having the following formula

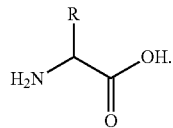

An α-amino acid may be naturally occurring or non-naturally occurring. Furthermore, an α-amino acid may have L or D stereochemistry. In some embodiments, the α-amino acid has L stereochemistry. In some embodiments, the α-amino acid has D stereochemistry. Examples of α-amino acids include, without limitation, glycine, alanine, valine, leucine, isoleucine, proline, tryptophan, phenylalanine, methionine, cysteine, tyrosine, serine, threonine, asparagine, glutamine, aspartic acid, glutamic acid, lysine, arginine, histidine, selenocysteine, hydroxyproline, and citrulline. As used herein, a "side chain of an α-amino acid" is the substituent R on the α-carbon of the α-amino acid.

In some embodiments, $R^1$ is a hydrophobic side chain. Examples of hydrophobic side chains include, without limitation, side chains of glycine, alanine, valine, leucine, isoleucine, proline, tryptophan, phenylalanine, methionine, cysteine, and tyrosine. In some embodiments, $R^1$ is a hydrophilic side chain. Examples of hydrophobic side chains include, without limitation, side chains of serine, threonine, asparagine, glutamine, aspartic acid, glutamic acid, lysine, arginine, histidine, selenocysteine, hydroxyproline, and citrulline. In some embodiments, $R^1$ is a side chain of an α-amino acid selected from the group consisting of glycine, alanine, valine, leucine, isoleucine, proline, tryptophan, phenylalanine, methionine, cysteine, and tyrosine. In some embodiments, $R^1$ is a side chain of an α-amino acid selected from the group consisting of serine, threonine, asparagine, glutamine, aspartic acid, glutamic acid, lysine, arginine, histidine, selenocysteine, hydroxyproline, and citrulline.

In some embodiments, $R^2$ is a hydrophobic side chain. In some embodiments, $R^2$ is a hydrophilic side chain. In some embodiments, $R^2$ is a side chain of an α-amino acid selected from the group consisting of glycine, alanine, valine, leucine, isoleucine, proline, tryptophan, phenylalanine, methionine, cysteine, and tyrosine. In some embodiments, $R^2$ is a side chain of an α-amino acid selected from the group consisting of serine, threonine, asparagine, glutamine, aspartic acid, glutamic acid, lysine, arginine, histidine, selenocysteine, hydroxyproline, and citrulline.

In some embodiments, $R^1$ and $R^2$ are both hydrophobic side chains. In some embodiments, R is a hydrophilic side chain and $R^2$ is a hydrophobic side chain. In some embodiments, R is a hydrophobic side chain and $R^2$ is a hydrophilic side chain. In some embodiments, $R^1$ and $R^2$ are both hydrophilic side chains. In some embodiments, $R^1$ is a side chain of an α-amino acid selected from the group consisting of glycine, alanine, valine, leucine, isoleucine, proline, tryptophan, phenylalanine, methionine, cysteine, and tyrosine; and $R^2$ is a side chain of an α-amino acid selected from the group consisting of serine, threonine, asparagine, glutamine, aspartic acid, glutamic acid, lysine, arginine, histidine, selenocysteine, hydroxyproline, and citrulline.

In some embodiments, provided herein is a method of preparing a compound of Formula (1A):

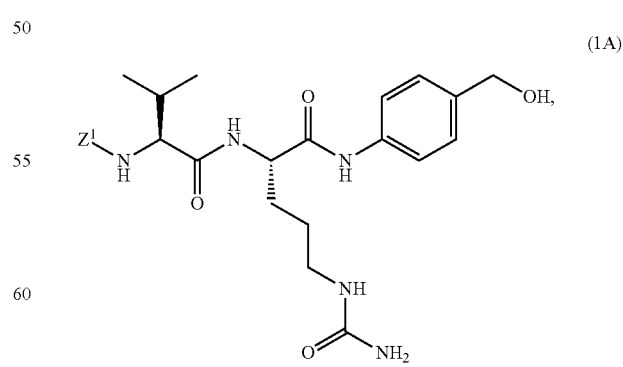

(1A)

or a salt thereof,
wherein $Z^1$ is a protecting group;

the method including reacting a compound of Formula (1B) or a salt thereof:

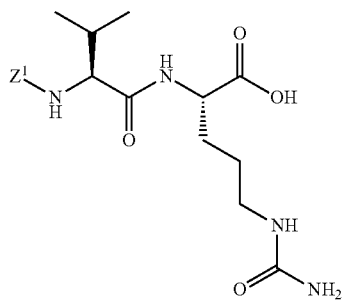

(1B)

with p-aminobenzyl alcohol (PABOH) in the presence of a peptide coupling reagent, wherein the peptide coupling reagent includes

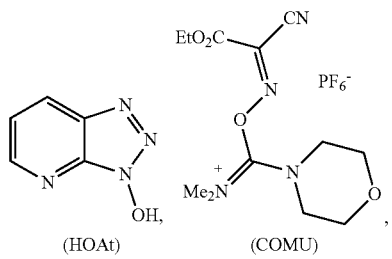

(HOAt)    (COMU)

or an HOAt derivative.

In some embodiments of any variation of the compound of Formula (1A) or (1A'), $Z^1$ is a protecting group. Examples of protecting groups include, without limitation, acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenylmethyloxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. In some embodiments, $Z^1$ is an alkoxy-carbonyl or aryloxy-carbonyl group. In some embodiments, $Z^1$ is selected from the group consisting of formyl, acetyl, benzoyl, pivaloyl, t-butylacetyl, phenylsulfonyl, Alloc, Teoc, benzyl, Fmoc, Boc and Cbz. In some embodiments, $Z^1$ is Fmoc.

As used herein an "HOAt derivative" is a compound having a

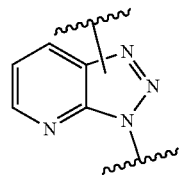

moiety, or a salt thereof. In some embodiments, the HOAt derivative is a compound having the following structure:

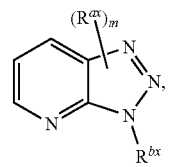

or a salt thereof, wherein $R^{ax}$ is selected from the group consisting of —S⁻ and —O⁻;

$R^{bx}$ is selected from the group consisting of

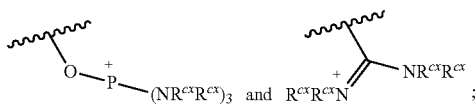

each $R^{cx}$ is independently alkyl or is taken together with the geminal $R^{cx}$ and the nitrogen to which it is attached to form a heterocyclyl group; and m is 0, or 1;

wherein when m is 1, the nitrogen to which $R^{ax}$ is attached is positively charged.

In some embodiments, each $R^{cx}$ is alkyl. In some embodiments, each $R^{cx}$ is methyl. In some embodiments, at least one pair of geminal $R^{cx}$ groups is taken together with the nitrogen to which they are attached to form a pyrrolidine ring. In some embodiments, each pair of geminal $R^{cx}$ groups is taken together with the nitrogen to which they are attached to form a pyrrolidinyl ring. In some embodiments, $R^{bx}$ is

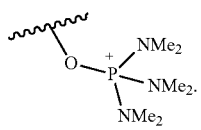

In some embodiments, $R^{bx}$ is

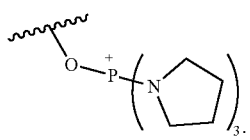

In some embodiments, $R^{bx}$ is

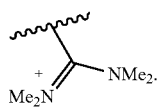

In some embodiments, the HOAt derivative is a hexafluorophosphate salt or a tetrafluoroborate salt. In some embodiments, the HOAt derivative is a hexafluorophosphate salt. In some embodiments, the HOAt derivative is a tetrafluoroborate salt. Examples of HOAt derivatives include, without limitation,

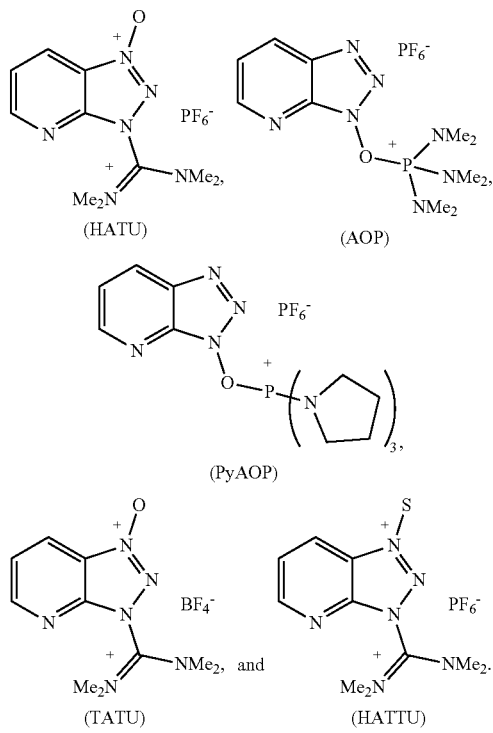

HOBt has the formula of

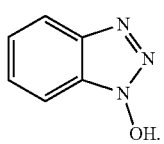

As used herein, an "HOBt derivative" is a compound having a

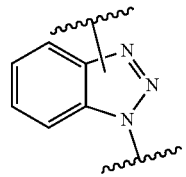

moiety or a salt thereof. In some embodiments, the HOBt derivative is a compound having the following structure:

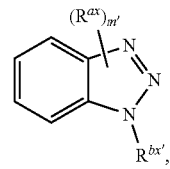

or a salt thereof, wherein
$R^{ax'}$ is selected from the group consisting of —S⁻ and —O⁻;
$R^{bx'}$ is selected from the group consisting of

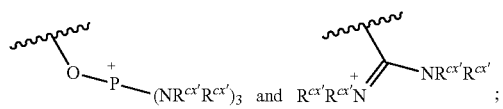

each $R^{cx'}$ is independently alkyl or is taken together with the geminal $R^{cx'}$ and the nitrogen to which it is attached to form a heterocyclyl group; and
m' is 0, or 1;
wherein when m is 1, the nitrogen to which $R^{ax'}$ is attached is positively charged.

In some embodiments, each $R^{cx'}$ is alkyl. In some embodiments, each $R^{cx'}$ is methyl. In some embodiments, at least one pair of geminal $R^{cx'}$ groups is taken together with the nitrogen to which they are attached to form a pyrrolidinyl ring. In some embodiments, each pair of geminal $R^{cx'}$ groups is taken together with the nitrogen to which they are attached to form a pyrrolidinyl ring. In some embodiments, $R^{bx'}$ is

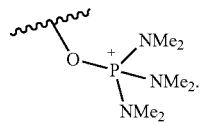

In some embodiments, $R^{bx'}$ is

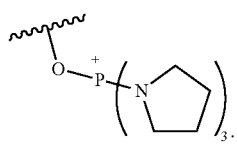

In some embodiments $R^{bx'}$ is

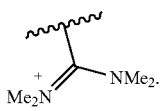

In some embodiments, the HOBt derivative is a hexafluorophosphate salt or a tetrafluoroborate salt. In some embodiments, the HOBt derivative is a hexafluorophosphate salt. In some embodiments, the HOBt derivative is a tetrafluoroborate salt. Examples of HOBt derivatives include, without limitation,

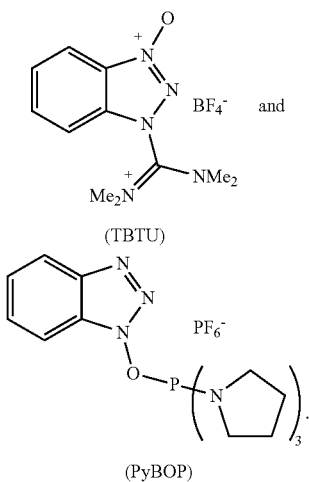

In some embodiments, the peptide coupling reagent contains a compound selected from the group consisting of HOAt, HATU, AOP, PyAOP, TATU, COMU, and HATTU. In some embodiments, the peptide coupling reagent contains HOAt. In some embodiments, the peptide coupling reagent contains an HOAt derivative. In some embodiments, the peptide coupling reagent contains HATU. In some embodiments, the peptide coupling reagent contains COMU. In some embodiments, the peptide coupling reagent contains AOP. In some embodiments, the peptide coupling reagent contains PyAOP. In some embodiments, the peptide coupling reagent contains TATU. In some embodiments, the peptide coupling reagent contains HATTU.

In some embodiments, the peptide coupling reagent contains HOAt and HOBt. In some embodiments, the peptide coupling reagent contains HOAt and a HOBt derivative. In some embodiments, the peptide coupling reagent contains HOAt and TBTU. In some embodiments, the peptide coupling reagent contains HOAt and PyBOP. In some embodiments, the peptide coupling reagent contains an HOAt derivative and HOBt. In some embodiments, the peptide coupling reagent contains an HOAt derivative and an HOBt derivative.

In some embodiments, the reaction of the compound of Formula (1B), (1B'), or any variation thereof, with the PABOH is performed in the presence of a base. In some embodiments, the base is an inorganic base. Examples of inorganic bases include, without limitation, potassium carbonate, sodium carbonate, cesium carbonate, potassium bicarbonate, sodium bicarbonate, sodium hydroxide, potassium hydroxide, magnesium hydroxide, and lithium hydroxide. In some embodiments, the base is an organic base. Examples of organic bases include, without limitation, N,N-Diisopropylethylamine (DIPEA), methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine and N-methylglucamine. In some embodiments, the base is any compatible mixture of bases such as those given as examples herein. In some embodiments, the base is DIPEA. The use of DIPEA may result in reduced formation of diastereomers and impurities.

In some embodiments, the reaction of the compound of Formula (1B), (1B'), or any variation thereof, with the PABOH is performed in an organic solvent. Examples of organic solvents includes, without limitations, hexane, pentane, cyclopentane, cyclohexane, benzene, toluene, 1,4-dioxane, chloroform, ethyl acetate, tetrahydrofuran (THF), dichloromethane, acetone, acetonitrile (MeCN), dimethylformamide (DMF), dimethyl sulfoxide (DMSO), 1,3-dimethyl-2-imidazolidinone (DMI), acetic acid, n-butanol, isopropanol, n-propanol, ethanol, and methanol. In some embodiments, the organic solvent is any compatible mixture of solvents such as those given as examples herein. In some embodiments, the organic solvent is free of water. In some embodiments, the organic solvent contains water.

In some embodiments, the reaction of the compound of Formula (1B), (1B'), or any variation thereof, with the PABOH is performed in an organic solvent. In some embodiments, the organic solvent contains DMF. In some embodiments, the organic solvent contains DMF and ethyl acetate. In some embodiments, the volume ratio of the DMF to the ethyl acetate is about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4.5:1, about 4:1, about 3.5:1, about 3:1, about 2.5:1, about 2:1, about 1.5:1, about 1:1, about 1:1.5, about 1:2, about 1:2.5, about 1:3, about 1:3.5, about 1:4, about 1:4.5, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100. In some embodiments, the volume ratio of the DMF to the ethyl acetate is no more than about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4.5:1, about 4:1, about 3.5:1, about 3:1, about 2.5:1, about 2:1, about 1.5:1, about 1:1, about 1:1.5, about 1:2, about 1:2.5, about 1:3, about 1:3.5, about 1:4, about 1:4.5, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100. In some embodiments, the volume ratio of the DMF to the ethyl acetate is at least about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4.5:1, about 4:1, about 3.5:1, about 3:1, about 2.5:1, about 2:1, about 1.5:1, about 1:1, about 1:1.5, about 1:2, about 1:2.5, about 1:3, about 1:3.5, about 1:4, about 1:4.5, about 1:5, about 1:6, about 1:7, about 1:8, about 1:9, about 1:10, about 1:20, about 1:30, about 1:40, about 1:50, about 1:60, about 1:70, about 1:80, about 1:90, or about 1:100. In some embodiments, the volume ratio of the DMF to the ethyl acetate is between about 5:1 and about 1:5, between about 4:1 and about 1:4, between about 3:1 and about 1:3, between about 2:1 and about 1:2, or between about 1.5:1 and about 1:1.5. In some embodiments, the volume ratio of the DMF to the ethyl acetate is about 1:1.

In some embodiments, the reaction of the compound of Formula (1B), (1B'), or any variation thereof, with the PABOH is performed at a temperature of no more than about 50° C., about 45° C., about 40° C., about 35° C., about 30° C., about 25° C., about 20° C., about 15° C., about 10° C., about 5° C., about 0° C., about −10° C., about −15° C., about −20° C., about −25° C., or about −30° C. In some embodiments, the reaction of the compound of Formula (1B), (1B'), or any variation thereof, with the PABOH is performed at a temperature of at least about 50° C., about 45° C., about 40° C., about 35° C., about 30° C., about 25° C., about 20° C., about 15° C., about 10° C., about 5° C., about 0° C., about −10° C., about −15° C., about −20° C., about −25° C., or about −30° C. In some embodiments, the reaction of the compound of Formula (1B), (1B'), or any variation thereof, with the PABOH is performed at a temperature of about 50° C., about 45° C., about 40° C., about 35° C., about 30° C., about 25° C., about 20° C., about 15° C., about 10° C., about 5° C., about 0° C., about −10° C., about −15° C., about −20° C., about −25° C., or about −30° C. In some embodiments, the reaction of the compound of Formula (1B), (1B'), or any variation thereof, with the PABOH is performed at a temperature of between about 20° C. and about −20° C., between about 15° C. and about −20° C., between about 10° C. and about −20° C., between about 5° C. and about −20° C., between about 20° C. and about −10° C., between about 15° C. and about −10° C., between about 10° C. and about −10° C., between about 5° C. and about −10° C., between about 20° C. and about −5° C., between about 15° C. and about −5° C., between about 10° C. and about −5° C., or between about 5° C. and about −5° C. In some embodiments, the reaction of the compound of Formula (1B), (1B'), or any variation thereof, with the PABOH is performed at a temperature of about 0° C. In some embodiments, the reaction of the compound of Formula (1B), (1B'), or any variation thereof, with the PABOH is performed at a temperature of no more than about 5° C.

In some embodiments, for the reaction of the compound of Formula (1B), (1B'), or any variation thereof, with the PABOH, the PABOH is mixed with the compound of Formula (1B) or Formula (1B') before addition of the DIPEA. In some embodiments, for the reaction of the compound of Formula (1B), (1B'), or any variation thereof, with the PABOH, the PABOH is mixed with DIPEA before addition of the compound of Formula (1B), (1B'), or any variation thereof. In some embodiments, for the reaction of the compound of Formula (1B), (1B'), or any variation thereof, with the PABOH, the PABOH is mixed with DIPEA before addition of the compound of Formula (1B), (1B'), or any variation thereof.

In some embodiments, for the reaction of the compound of Formula (1B), (1B'), or any variation thereof, with the PABOH, the PABOH is mixed with the compound of Formula (1B), (1B'), or any variation thereof, before addition of the base (e.g., DIPEA) and the base (e.g., DIPEA) is added about 0.1 minutes, about 0.5 minutes, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, about 40 minutes, about 50 minutes, about 60 minutes after the PABOH is mixed with the compound of Formula (1B), (1B'), or any variation thereof. In some embodiments, for the reaction of the compound of Formula (1B), (1B'), or any variation thereof, with the PABOH, the PABOH is mixed with the compound of Formula (1B), (1B'), or any variation thereof, before addition of the base (e.g., DIPEA) and the base (e.g., DIPEA) is added no more than about 0.1 minutes, about 0.5 minutes, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, about 40 minutes, about 50 minutes, about 60 minutes after the PABOH is mixed with the compound of Formula (1B), (1B'), or any variation thereof. In some embodiments, for the reaction of the compound of Formula (1B), (1B'), or any variation thereof, with the PABOH, the PABOH is mixed with the compound of Formula (1B), (1B'), or any variation thereof, before addition of the base (e.g., DIPEA) and the base (e.g., DIPEA) is added between about 0.1 minutes and about 60 minutes, between about 0.1 minutes and about 50 minutes, between about 0.1 minutes and about 40 minutes, between about 0.1 minutes and about 30 minutes, between about 0.1 minutes and about 20 minutes, between about 0.1 minutes and about 10 minutes, between about 0.1 minutes and about 5 minutes, between about 0.1 minutes and about 1 minute, between about 0.5 minutes and about 60 minutes, between about 0.5 minutes and about 50 minutes, between about 0.5 minutes and about 40 minutes, between about 0.5 minutes and about 30 minutes, between about 0.5 minutes and about 20 minutes, between about 0.5 minutes and about 10 minutes, between about 0.5 minutes and about 5 minutes, between about 0.5 minutes and about 1 minute, between about 1 minutes and about 60 minutes, between about 1 minutes and about 50 minutes, between about 1 minutes and about 40 minutes, between about 1 minutes and about 30 minutes, between about 1 minutes and about 20 minutes, between about 1 minutes and about 10 minutes, between about 1 minutes and about 5 minutes, between about 5 minutes and about 60 minutes, between about 5 minutes and about 50 minutes, between about 5 minutes and about 40 minutes, between about 5 minutes and about 30 minutes, between about 5 minutes and about 20 minutes, or between about 5 minutes and about 10 minutes, after the PABOH is mixed with the compound of Formula (1B), (1B'), or any variation thereof. In some embodiments, for the reaction of the compound of Formula (1B), (1B'), or any variation thereof, with the PABOH, the PABOH is mixed with the compound of Formula (1B), (1B'), or any variation thereof, before addition of the base (e.g., DIPEA) and the base (e.g., DIPEA) is added no more than about 5 minutes after the PABOH is mixed with the compound of Formula (1B), (1B'), or any variation thereof.

In some embodiments, the compound of formula (1B') is obtained by reacting a compound of Formula (1C') or a salt thereof:

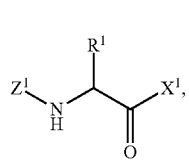
(1C')

wherein $X^1$ is a carboxyl-activating group; and $Z^1$ and R are as defined herein, with

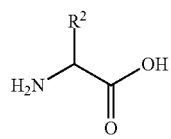

or a salt thereof, wherein $R^2$ is as defined herein, to form the compound of Formula (1B') or a salt thereof.

In some embodiments, the compound of formula (1B) is obtained by reacting a compound of Formula (1C) or a salt thereof:

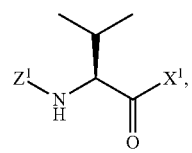
(1C)

wherein $Z^1$ is as defined herein; and $X^1$ is a carboxyl-activating group, with

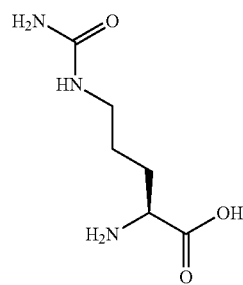

or a salt thereof, to form the compound of Formula (1B) or a salt thereof.

In some embodiments, $X^1$ is

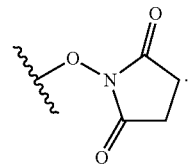 [SMILES: *ON1C(=O)CCC1=O]

In some embodiments, the compound of Formula (1A') or a salt thereof is further converted to a compound of Formula (1D') or a salt thereof:

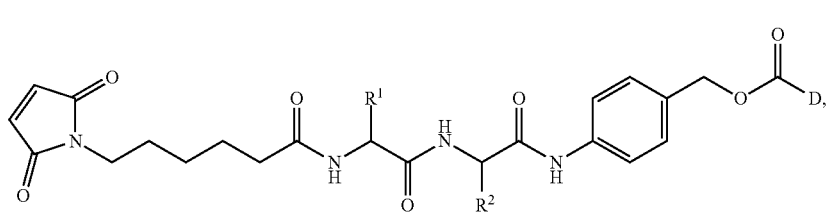
(1D')

wherein $R^1$ and $R^2$ are as defined herein; and D is a moiety of Formula (D):

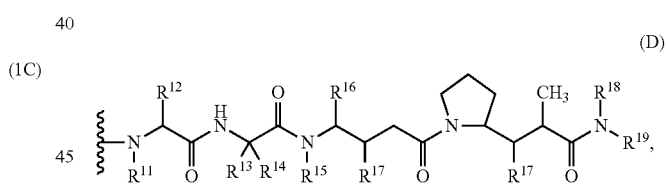
(D)

wherein the wavy line indicates covalent bonding of D to the remainder of the compound;

$R^{11}$ is selected from the group consisting of H and $C_1$-$C_8$ alkyl;

$R^{12}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);

$R^{13}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);

$R^{14}$ is selected from the group consisting of H and methyl; or $R^{13}$ and $R^{14}$ jointly form a carbocyclic ring and have the formula —$(CR^aR^b)_n$—, wherein $R^a$ and $R^b$ are independently selected from the group consisting of H, $C_1$-$C_8$ alkyl and $C_3$-$C_8$ carbocyclyl, and n is selected from the group consisting of 2, 3, 4, 5 and 6;

$R^{15}$ is selected from the group consisting of H and $C_1$-$C_8$ alkyl;

$R^{16}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);

each $R^{17}$ is independently selected from the group consisting of H, OH, $C_1$-$C_8$ alkyl, $C_3$-$C_8$ carbocyclyl, and —O—($C_1$-$C_8$ alkyl);

$R^{18}$ is selected from the group consisting of H and $C_1$-$C_5$ alkyl;

$R^{19}$ is selected from the group consisting of —C($R^{17}$)$_2$—C($R^{17}$)$_2$-aryl, —C($R^{17}$)$_2$—C($R^{17}$)$_2$—($C_3$-$C_8$ heterocyclyl), —C($R^{17}$)$_2$—C(O)—Z$R^{20}$, and —C($R^{17}$)$_2$—C($R^{17}$)$_2$—($C_3$-$C_8$ carbocyclyl);

$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl; and Z is —O—, or —NH—, or Z— is —O— and $R^{20}$ is $C_1$-$C_4$ alkyl or Z is —NH— and $R^{20}$ is optionally substituted phenyl or optionally substituted $C_5$-$C_6$ heteroaryl.

In some embodiments, the compound of Formula (1A) or a salt thereof is further converted to a compound of Formula (1D) or a salt thereof:

alkyl-($C_3$-$C_8$ carbocyclyl), $C_3$-$C_8$ heterocyclyl, and $C_1$-$C_8$ alkyl-($C_3$-$C_8$ heterocyclyl);

$R^{13}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);

$R^{14}$ is selected from the group consisting of H and methyl;

or $R^{13}$ and $R^{14}$ jointly form a carbocyclic ring and have the formula —(CR$^a$R$^b$)$_n$—, wherein $R^a$ and $R^b$ are independently selected from the group consisting of H, $C_1$-$C_8$ alkyl and $C_3$-$C_8$ carbocyclyl, and n is selected from the group consisting of 2, 3, 4, 5 and 6;

$R^{15}$ is selected from the group consisting of H and $C_1$-$C_8$ alkyl;

$R^{16}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);

each $R^{17}$ is independently selected from the group consisting of H, OH, $C_1$-$C_8$ alkyl, $C_3$-$C_8$ carbocyclyl, and —O—($C_1$-$C_8$ alkyl);

$R^{18}$ is selected from the group consisting of H and $C_1$-$C_8$ alkyl;

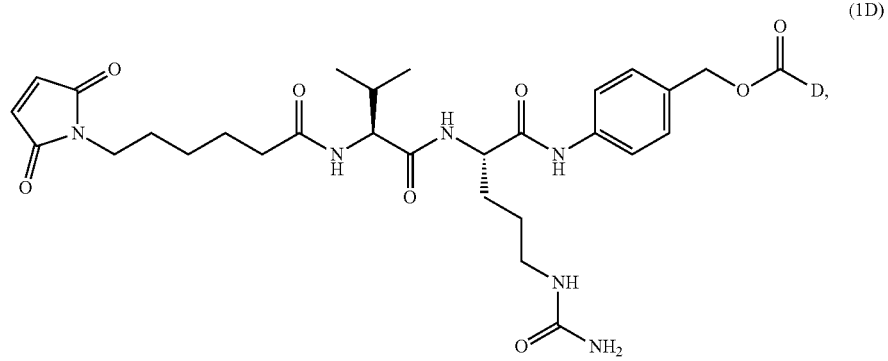

(1D)

wherein D is a moiety of Formula (D):

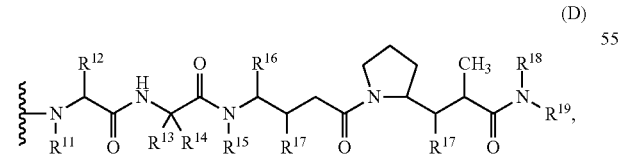

(D)

wherein the wavy line indicates covalent bonding of D to the remainder of the compound;

$R^{11}$ is selected from the group consisting of H and $C_1$-$C_8$ alkyl;

$R^{12}$ is selected from the group consisting of H, $C_1$-$C_8$ alkyl, $C_3$-$C_8$ carbocyclyl, aryl, $C_1$-$C_8$ alkyl-aryl, $C_1$-$C_8$ $R^{19}$ is selected from the group consisting of —C($R^{17}$)$_2$—C($R^{17}$)$_2$-aryl, —C($R^{17}$)$_2$—C($R^{17}$)$_2$—($C_3$-$C_8$ heterocyclyl), —C($R^{17}$)$_2$—C(O)—Z$R^{20}$, and —C($R^{17}$)$_2$—C($R^{17}$)$_2$—($C_3$-$C_8$ carbocyclyl);

$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl; and Z is —O—, or —NH—, or Z— is —O— and $R^{20}$ is $C_1$-$C_4$ alkyl or Z is —NH— and $R^{20}$ is optionally substituted phenyl or optionally substituted $C_5$-$C_6$ heteroaryl.

In some embodiments of the compound of Formula (1D), (1D'), or any variation thereof, D is a moiety of any one of Formulae $D_{E-1}$, $D_{E-2}$, $D_{F-1}$ and $D_{F/E-3}$:

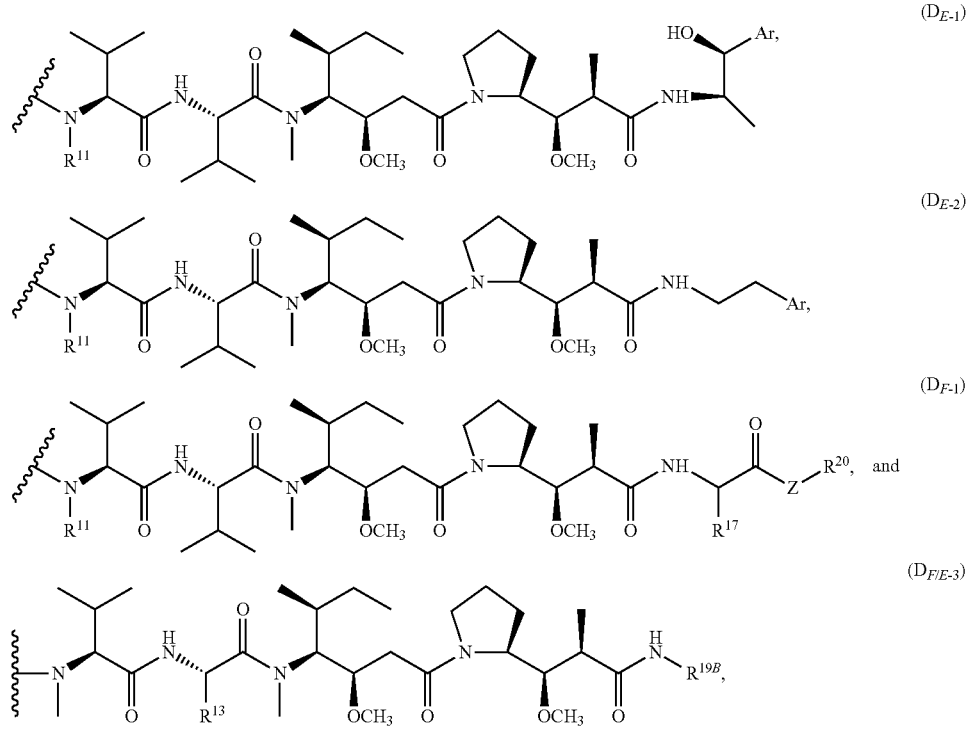

wherein the wavy line indicates covalent bonding of D to the remainder of the compound;

$R^{11}$ is selected from the group consisting of H and $C_1$-$C_8$ alkyl;

$R^{13}$ is isopropyl or —$CH_2$—$CH(CH_3)_2$;

$R^{17}$ is selected from the group consisting of H, OH, $C_1$-$C_8$ alkyl, $C_3$-$C_8$ carbocyclyl, and —O—($C_1$-$C_8$ alkyl);

$R^{19B}$ is —$CH(CH_3)$—$CH(OH)Ph$, —$CH(CO_2H)CH_2Ph$, —$CH(CH_2Ph)$-2-thiazole, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, $CH(CH_2CH_2SCH_3)C(=O)NH$-3-quinolyl, or —$CH(CH_2Ph)C(=O)NH$-p-Cl-Ph;

$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl; and Ar is optionally substituted $C_6$-$C_{10}$ aryl or optionally substituted $C_3$-$C_8$ heterocyclyl.

In some embodiments of the compound of Formula (1D), (1D'), or any variation thereof, D is a moiety of Formula (D1):

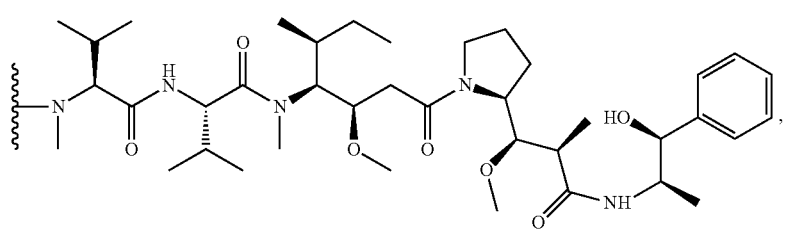

wherein the wavy line indicates covalent bonding of D to the remainder of the compound.

In some embodiments, the conversion of the compound of Formula (1A') or a salt thereof to the compound of Formula (1D') or a salt thereof includes converting the compound of Formula (1A') or a salt thereof to a compound of Formula (1E') or a salt thereof:

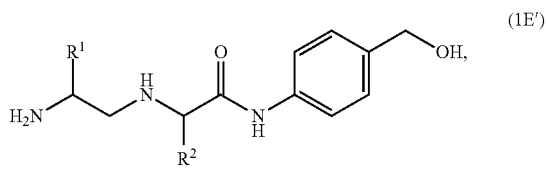

wherein $R^1$ and $R^2$ are as defined herein,
and converting the compound of Formula (1E') or a salt thereof to a compound of Formula (1D') or a salt thereof.

In some embodiments, the conversion of the compound of Formula (1A) or a salt thereof to the compound of Formula (1D) or a salt thereof includes converting the compound of Formula (1A) or a salt thereof to a compound of Formula (1E) or a salt thereof:

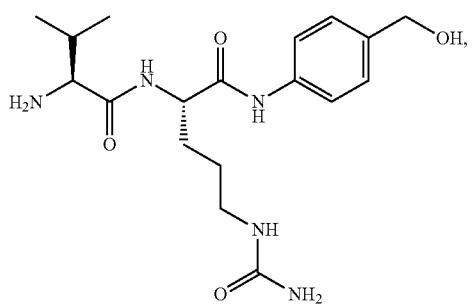
(1E)

and converting the compound of Formula (1E) or a salt thereof to a compound of Formula (1D) or a salt thereof.

In some embodiments, the conversion of the compound of Formula (1A') or a salt thereof to the compound of Formula (1D') or a salt thereof includes reacting the compound of Formula (1E') or a salt thereof with a compound of Formula (1F):

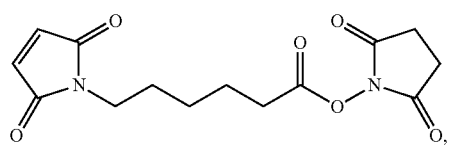
(1F)

to form a compound of Formula (1G') or a salt thereof:

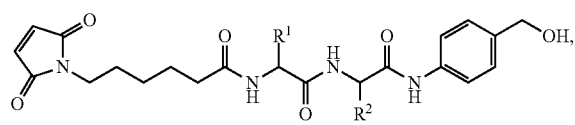
(1G')

wherein R¹ and R² are as defined herein,
and converting the compound of Formula (1G') or a salt thereof to the compound of Formula (1D') or a salt thereof.

In some embodiments, the conversion of the compound of Formula (1A) or a salt thereof to the compound of Formula (1D) or a salt thereof includes reacting the compound of Formula (1E) or a salt thereof with a compound of Formula (1F):

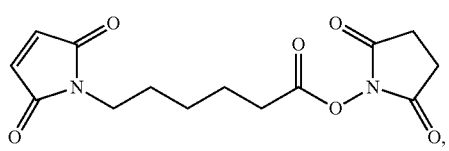
(1F)

to form a compound of Formula (1G) or a salt thereof:

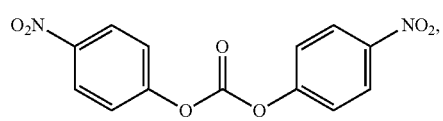
(1G)

and converting the compound of Formula (1G) or a salt thereof to the compound of Formula (1D) or a salt thereof.

In some embodiments, the conversion of the compound of Formula (1A') or a salt thereof to the compound of Formula (1D') or a salt thereof, further includes reacting the compound of Formula (1G') or a salt thereof with a compound of Formula (1H):

(1H)

$$O_2N\text{—}\bigcirc\text{—}O\text{—}C(=O)\text{—}O\text{—}\bigcirc\text{—}NO_2$$

to form a compound of Formula (1I') or a salt thereof:

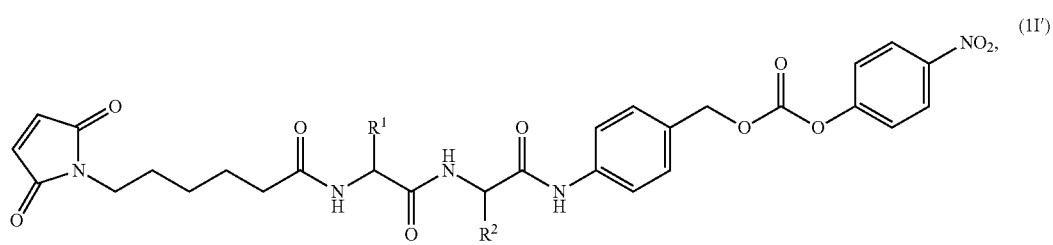
(1I')

wherein R¹ and R² are as defined herein,
and converting the compound of Formula (1I') or a salt thereof to the compound of Formula (1D') or a salt thereof.

In some embodiments, the conversion of the compound of Formula (1A) or a salt thereof to the compound of Formula (1D) or a salt thereof further includes reacting the compound of Formula (1G) or a salt thereof with a compound of Formula (1H):

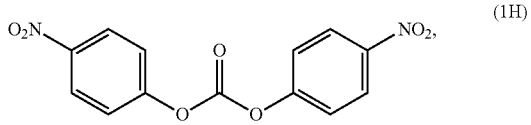 [SMILES: O=C(Oc1ccc([N+](=O)[O-])cc1)Oc1ccc([N+](=O)[O-])cc1]
(1H)

to form a compound of Formula (1I) or a salt thereof:

$R^{13}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);

$R^{14}$ is selected from the group consisting of H and methyl;

or $R^{13}$ and $R^{14}$ jointly form a carbocyclic ring and have the formula —$(CR^aR^b)_n$—, wherein $R^a$ and $R^b$ are independently selected from the group consisting of H, $C_1$-$C_8$ alkyl and $C_3$-$C_8$ carbocyclyl, and n is selected from the group consisting of 2, 3, 4, 5 and 6;

$R^{15}$ is selected from the group consisting of H and $C_1$-$C_8$ alkyl;

$R^{16}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);

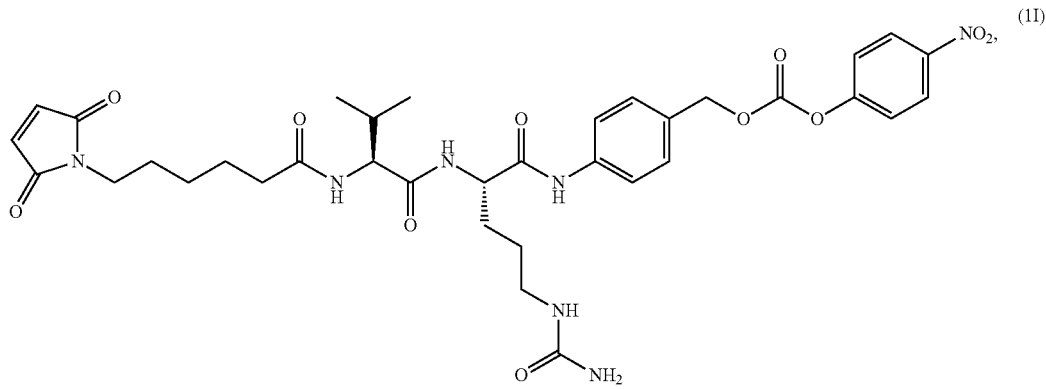 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]
(1I)

and converting the compound of Formula (1I) or a salt thereof to the compound of Formula (1D) or a salt thereof.

In some embodiments, the conversion of the compound of Formula (1A'), (1A), or a salt thereof to the compound of Formula (1D'), (1D), or a salt thereof further includes reacting the compound of Formula (1I'), (1I), or a salt thereof with a compound of Formula (1J):

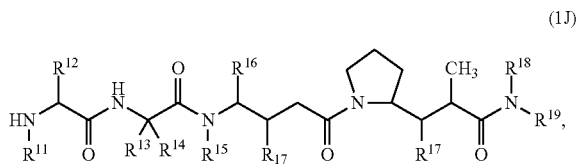
(1J)

wherein
$R^{11}$ is selected from the group consisting of H and $C_1$-$C_8$ alkyl;
$R^{12}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);

each $R^{17}$ is independently selected from the group consisting of H, OH, $C_1$-$C_8$ alkyl, $C_3$-$C_8$ carbocyclyl, and —O—($C_1$-$C_8$ alkyl);

$R^{18}$ is selected from the group consisting of H and $C_1$-$C_8$ alkyl;

$R^{19}$ is selected from the group consisting of —$C(R^{17})_2$—$C(R^{17})_2$-aryl, —$C(R^{17})_2$—$C(R^{17})_2$—($C_3$-$C_8$ heterocyclyl), —$C(R^{17})_2$—$C(O)$—$ZR^{20}$, and —$C(R^{17})_2$—$C(R^{17})_2$—($C_3$-$C_8$ carbocyclyl);

$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl; and Z is —O—, or —NH—, or Z— is —O— and $R^{20}$ is $C_1$-$C_4$ alkyl or Z is —NH— and $R^{20}$ is optionally substituted phenyl or optionally substituted $C_5$-$C_6$ heteroaryl, to form the compound of Formula (1D'), (1D), or a salt thereof.

In some embodiments, the compound of formula (1J) is of any one of Formulae $1J_{E-1}$, $1J_{E-2}$, $1J_{F-1}$ and $1J_{F/E-3}$.

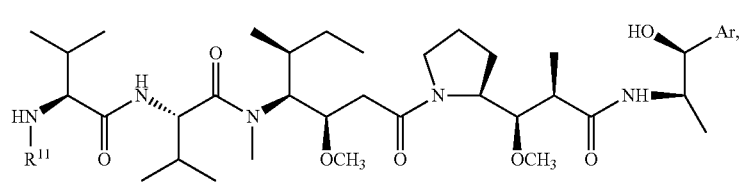

(1J<sub>E-1</sub>)

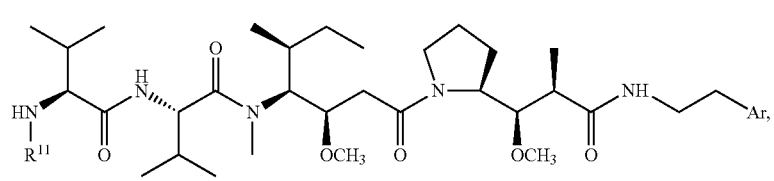

(1J<sub>E-2</sub>)

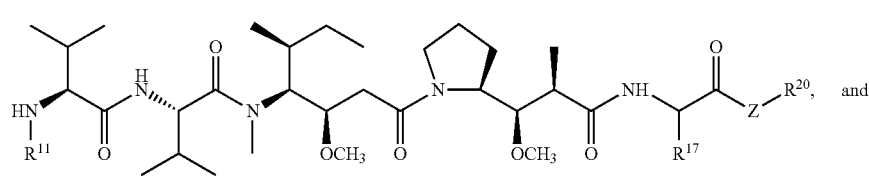

(1J<sub>F-1</sub>)

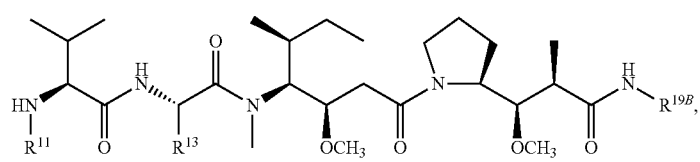

(1J<sub>F/E-3</sub>)

wherein $R^{11}$ is selected from the group consisting of H and $C_1$-$C_8$ alkyl;

$R^{13}$ is isopropyl or —CH$_2$—CH(CH$_3$)$_2$;

$R^{17}$ is selected from the group consisting of H, OH, $C_1$-$C_8$ alkyl, $C_3$-$C_8$ carbocyclyl, and —O—($C_1$-$C_5$ alkyl);

$R^{19B}$ is —CH(CH$_3$)—CH(OH)Ph, —CH(CO$_2$H)CH$_2$Ph, —CH(CH$_2$Ph)-2-thiazole, —CH(CH$_2$Ph)-2-pyridyl, —CH(CH$_2$-p-Cl-Ph), —CH(CO$_2$Me)-CH$_2$Ph, —CH(CO$_2$Me)-CH$_2$CH$_2$SCH$_3$, CH(CH$_2$CH$_2$SCH$_3$)C(=O)NH-3-quinolyl, or —CH(CH$_2$Ph)C(=O)NH-p-Cl-Ph;

$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl; and Ar is optionally substituted $C_6$-$C_{10}$ aryl or optionally substituted $C_3$-$C_8$ heterocyclyl.

In some embodiments, the compound of Formula (1D') is further reacted with an antibody to form a compound of Formula (5'):

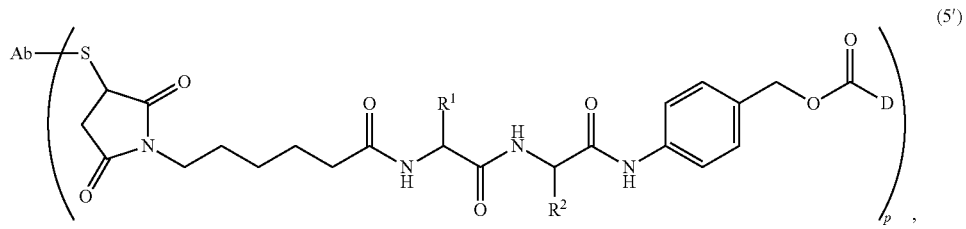

(5')

or a pharmaceutically acceptable salt thereof, wherein
R¹ and R² are as defined herein;
Ab is an antibody;
S is a sulfur atom from the antibody; and
p is an integer from 1 to 16, inclusive.

In some embodiments, the compound of Formula (1D) is further reacted with an antibody to form a compound of Formula (5):

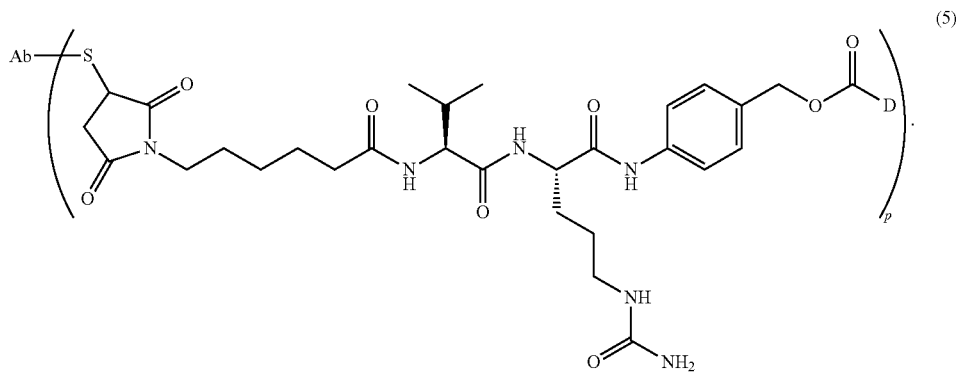

or a pharmaceutically acceptable salt thereof, wherein
Ab is an antibody;
S is a sulfur atom from the antibody; and
p is an integer from 1 to 16, inclusive.

In some embodiments of the compound of Formula (5), (5'), or any variation thereof, Ab is an anti-CD19 antibody, anti-CD70 antibody, anti-CD30 antibody, anti-CD33 antibody, anti-CD48 antibody, anti-NTB-A antibody, anti-avP6 antibody, anti-Nectin-4 antibody, anti-SLITRK6 antibody, anti-LIV1 antibody, or anti-CD123 antibody. In some embodiments, Ab is an anti-CD30 antibody. In some embodiments, Ab is monoclonal anti-CD19 antibody BU12. In some embodiments, Ab is a humanized monoclonal anti-CD19 antibody hBU12. In some embodiments, Ab is an anti-Nectin-4 antibody AGS-22C₃. In some embodiments, Ab is an anti-SLITRK6 antibody AGS15C. In some embodiments, Ab is monoclonal anti-LIV1 antibody LIV22. In some embodiments, Ab is a humanized monoclonal anti-LIV1 antibody hLIV22. In some embodiments, Ab is monoclonal anti-CD19 antibody BU12. In some embodiments, Ab is a humanized monoclonal anti-CD19 antibody hBU12. In some embodiments, Ab is monoclonal anti-CD30 antibody AC10. In some embodiments, Ab is a chimeric monoclonal anti-CD30 antibody cAC10.

In some embodiments of the compound of Formula (5), (5'), or any variation thereof, p is 1, 2, 3, 4, 5, 6, 7, 8, 9, 10, 11, 12, 13, 14, 15, or 16. In some embodiments, p is at least 1, 2, 3, 4, 5, 6, 7, 8, 9, 10, 11, 12, 13, 14, or 15. In some embodiments, p is no more than 2, 3, 4, 5, 6, 7, 8, 9, 10, 11, 12, 13, 14, 15, or 16. In some embodiments, p is between 1 and 16, between 1 and 10, between 1 and 5, between 5 and 16, between 5 and 10, or between 10 and 16. P may vary within a sample composition.

Compositions
In another aspect, provided herein is a compound of Formula (4), or a salt thereof:
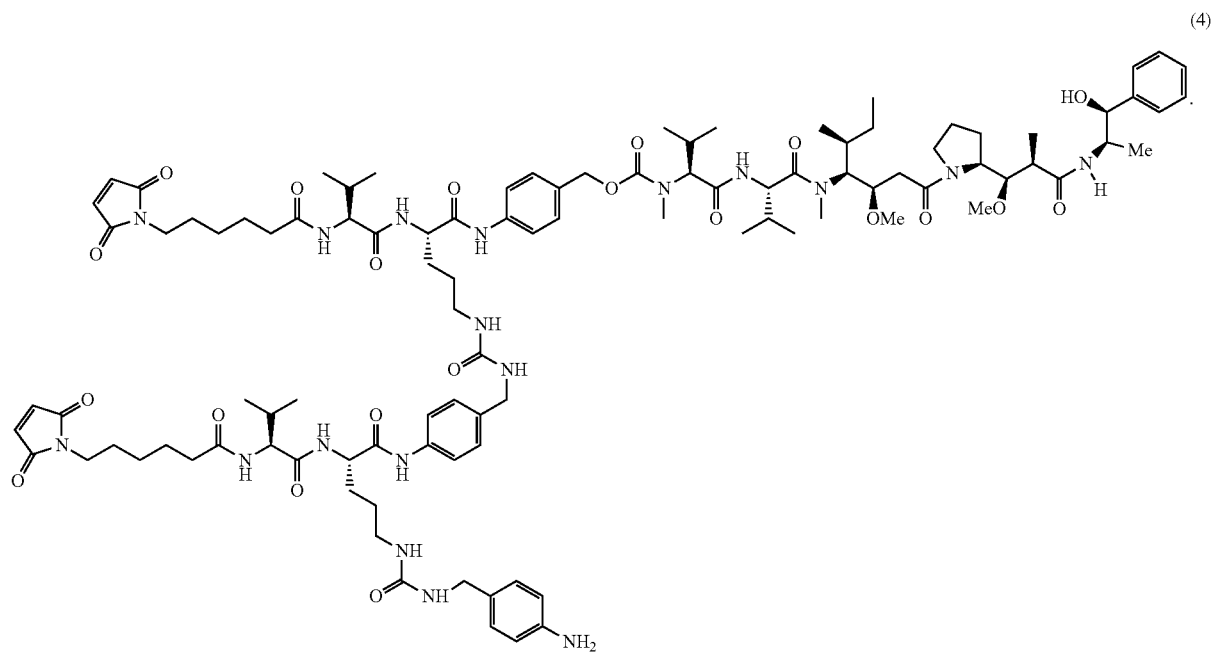 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(=O)NCc2ccc(NC(=O)[C@H](CCCNC(=O)NCc3ccc(N)cc3)NC(=O)[C@@H](NC(=O)CCCCCN3C(=O)C=CC3=O)C(C)C)cc2)NC(=O)[C@@H](NC(=O)CCCCCN2C(=O)C=CC2=O)C(C)C)cc1)C(C)C]
(4)
In another aspect, provided herein is a composition comprising a compound of Formula (3), or a salt thereof:
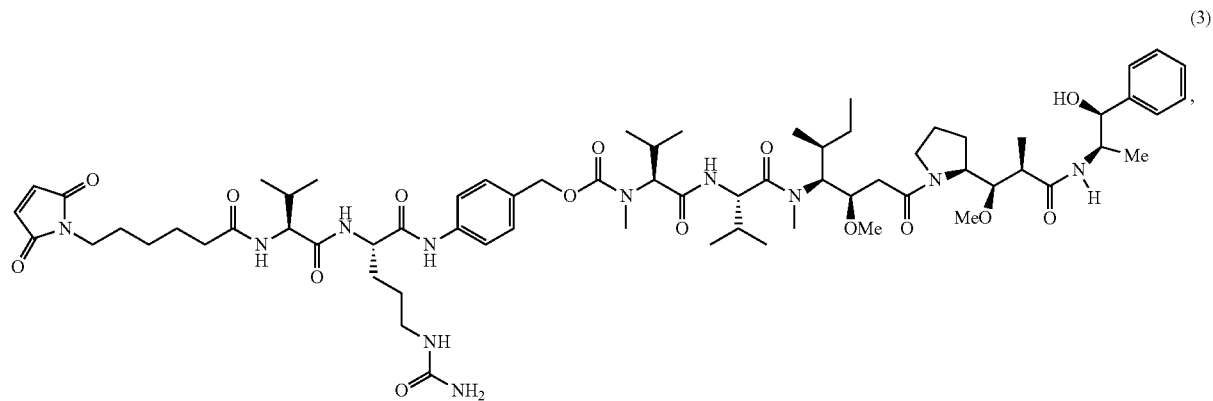 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]
(3)

and a compound of Formula (4), or a salt thereof:

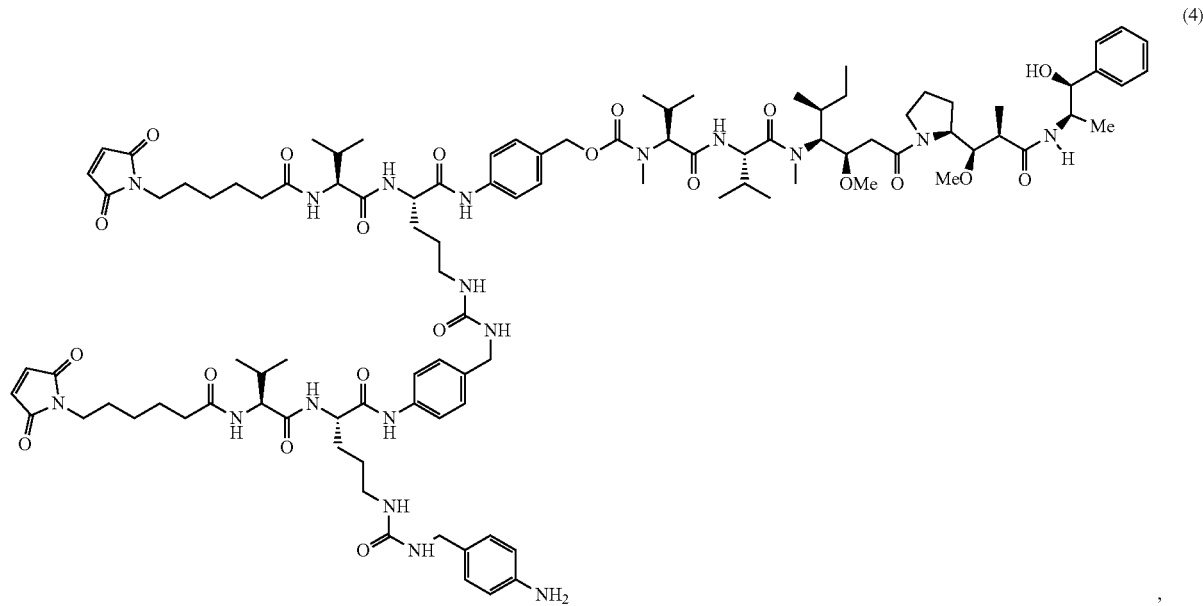 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(=O)NCc2ccc(NC(=O)[C@H](CCCNC(=O)NCc3ccc(N)cc3)NC(=O)[C@@H](NC(=O)CCCCCN3C(=O)C=CC3=O)C(C)C)cc2)NC(=O)[C@@H](NC(=O)CCCCCN2C(=O)C=CC2=O)C(C)C)cc1)C(C)C]

(4)

wherein the molar ratio of the compound of Formula (4) to the compound of Formula (3) is no more than about 10%, about 9%, about 8%, about 7%, about 7%, about 6%, about 5%, about 4%, about 3%, about 2%, about 1%, about 0.5%, about 0.1%, about 0.05%, about 0.01%, about 0.005%, about 0.001%, about 0.0005%, or about 0.0001%. In some embodiments, the molar ratio of the compound of Formula (4) to the compound of Formula (3) is no more than about 0.1%.

In another aspect, provided herein is a composition comprising a compound of Formula (3), or a salt thereof:

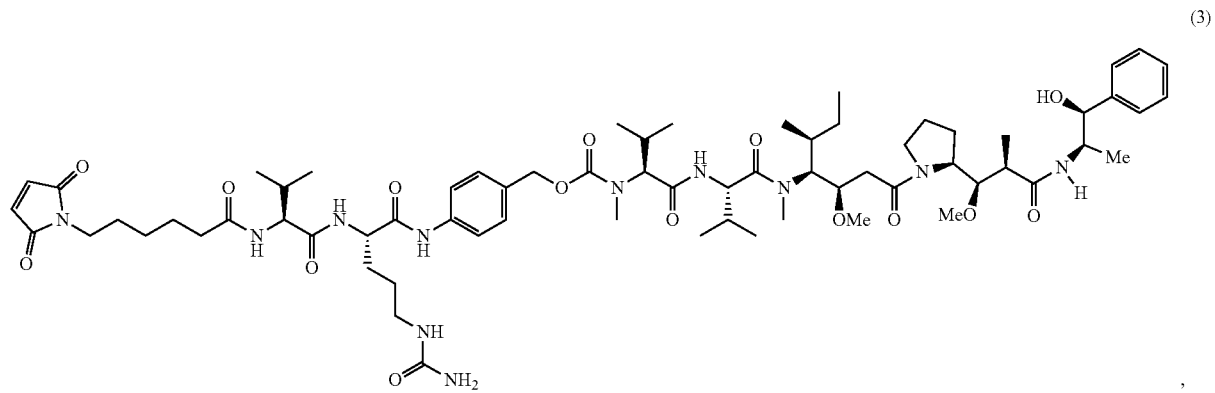 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

(3)

wherein the composition is substantially free of a compound of Formula (4):

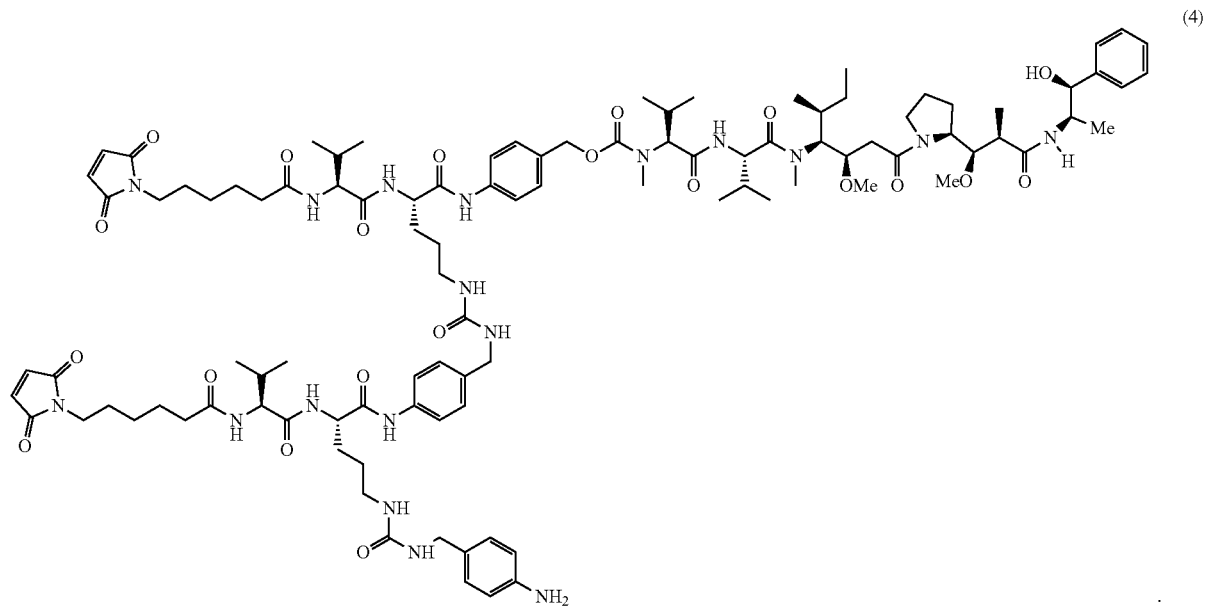 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(=O)NCc2ccc(NC(=O)[C@H](CCCNC(=O)NCc3ccc(N)cc3)NC(=O)[C@@H](NC(=O)CCCCCN3C(=O)C=CC3=O)C(C)C)cc2)NC(=O)[C@@H](NC(=O)CCCCCN2C(=O)C=CC2=O)C(C)C)cc1)C(C)C]

In another aspect, provided herein is a composition comprising a compound of Formula (5):

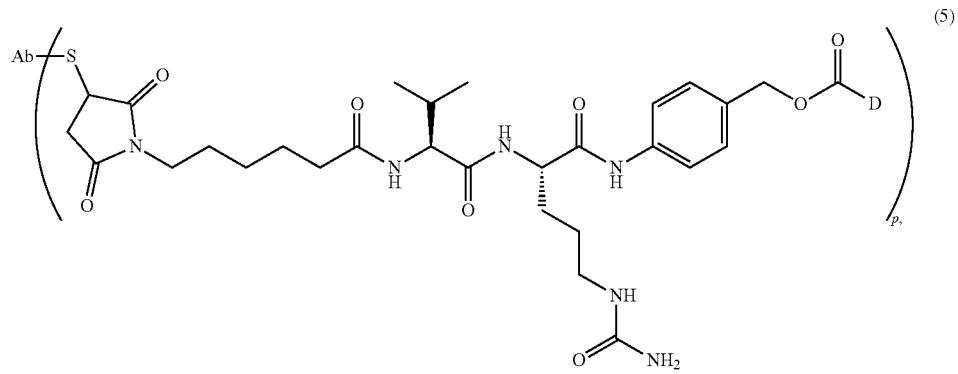

or a pharmaceutically acceptable salt thereof, wherein
Ab is an antibody;
S is a sulfur atom from the antibody;
D is a moiety of formula:

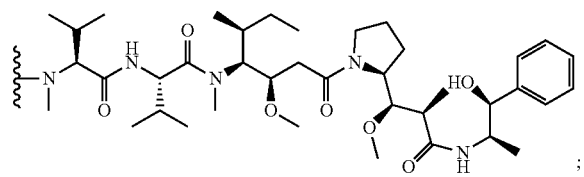 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

and
p is an integer from 1 to 16, inclusive,
wherein the composition is substantially free of the compound of Formula (4) or an adduct of the compound of Formula (4) with the antibody.

In some embodiments, Ab is an anti-CD19 antibody, anti-CD70 antibody, anti-CD30 antibody, anti-CD33 antibody, anti-CD48 antibody, anti-NTB-A antibody, anti-avP6 antibody, anti-Nectin-4 antibody, anti-SLITRK6 antibody, anti-LIV1 antibody, or anti-CD123 antibody. In some embodiments, Ab is monoclonal anti-CD19 antibody BU12. In some embodiments, Ab is a humanized monoclonal anti-CD19 antibody hBU12. In some embodiments, Ab is an anti-Nectin-4 antibody AGS-22C3. In some embodiments, Ab is an anti-SLITRK6 antibody AGS15C. In some embodiments, Ab is monoclonal anti-LIV1 antibody LIV22. In some embodiments, Ab is a humanized monoclonal anti-LIV1 antibody hLIV22. In some embodiments, Ab is monoclonal anti-CD19 antibody BU12. In some embodiments, Ab is a humanized monoclonal anti-CD19 antibody hBU12. In some embodiments, Ab is an anti-CD30 antibody. In some embodiments, Ab is monoclonal anti-CD30 antibody AC10. In some embodiments, Ab is chimeric monoclonal anti-CD30 antibody cAC10.

In some embodiments, p is 1, 2, 3, 4, 5, 6, 7, 8, 9, 10, 11, 12, 13, 14, 15, or 16. In some embodiments, p is at least 1, 2, 3, 4, 5, 6, 7, 8, 9, 10, 11, 12, 13, 14, or 15. In some embodiments, p is no more than 2, 3, 4, 5, 6, 7, 8, 9, 10, 11, 12, 13, 14, 15, or 16. In some embodiments, p is between 1 and 16, between 1 and 10, between 1 and 5, between 5 and 16, between 5 and 10, or between 10 and 16. Within a sample composition, p may vary between the compounds of Formula (5).

In some embodiments, the composition is substantially free of the compound of Formula (4). In some embodiments, the composition is substantially free of any adduct of the compound of Formula (4) with an antibody.

In some embodiments of any of the compositions provided herein, the composition further comprises a pharmaceutically acceptable carrier or excipient. The pharmaceutically acceptable carrier can be solid, semi-solid, or liquid material that acts as a vehicle, or medium for the compounds disclosed herein. Examples of pharmaceutically acceptable carriers include, without limitation, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the pharmaceutically acceptable carriers can include any sustained release material known in the art, such as glyceryl monostearate or glyceryl distearate, alone or mixed with a wax. The pharmaceutically acceptable excipient can be an inert or inactive substance that may be used in the production of a drug or pharmaceutical, such as a tablet containing a compound or composition provided herein as an active ingredient. Examples of pharmaceutically acceptable excipients, include, without limitation, any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, without limitation, carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Synthetic Schemes

Certain processes provided herein are described in reference to the illustrative synthetic scheme for the compound of Formula (3) shown below and the specific examples that follow. Certain reactions and conversions described herein can be conducted using methods known in the art. For example, Han et al. (*Tetrahedron* 2004, 60, 2447-2467) and Dubowchik et al. (*Bioconjugate Chem.* 2002, 13, 855-869) describe methods and reagents that can be used to synthesize certain compounds disclosed herein. Skilled artisans will recognize that, to obtain various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Abbreviations used herein are explained in the following table.

| Abbreviations | |
|---|---|
| Abbreviation | Meaning |
| DIPEA | N,N-diisopropyl-N-ethylamine |
| DMF | N,N-dimethylformamide |
| Fmoc | fluorenylmethyloxycarbonyl |
| Val | valine |
| HOSu | N-hydroxysuccinimide |
| Cit | citrulline |
| ACN | acetonitrile |
| EtOAc | ethyl acetate |
| PABOH | p-aminobenzyl alcohol |
| PNP | p-nitrophenyl |
| DMA | dimethylacetamide |
| THF | tetrahydrofuran |
| EDC | 1-ethyl-3-(3-dimethylaminopropyl)carbodiimide |
| NHS | N-hydroxysuccinimide |
| MS | mass spectrometry |
| mc | maleimidocaproyl |
| HPLC | high-performance liquid chromatography |
| EEDQ | 2-ethoxy-1-ethoxycarbonyl-1,2-dihydroquinoline; |
| MeOH | methanol |
| T3P | propylphoshonic anhydride |
| CDI | 1,1'-carbonyldiimidazole |
| LCMS | liquid chromatography mass spectrometry |

51
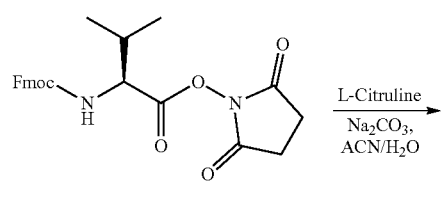
Fmoc-Val-OSu
L-Citruline
Na$_2$CO$_3$,
ACN/H$_2$O
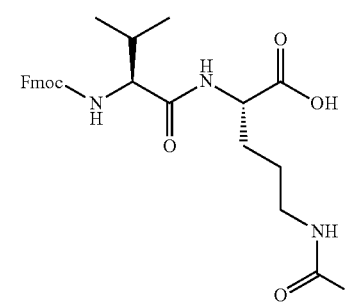
Fmoc-Val-Cit
52
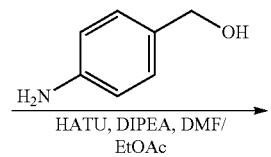
HATU, DIPEA, DMF/
EtOAc
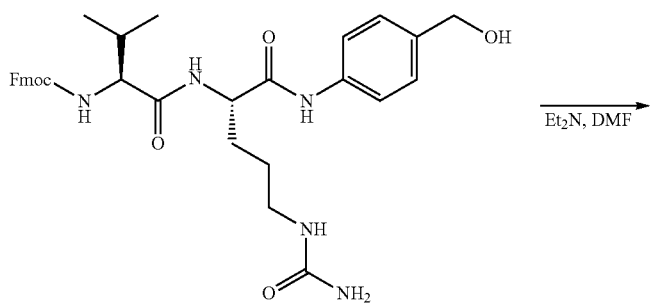
Fmoc-Val-Cit-PABOH
Et$_2$N, DMF
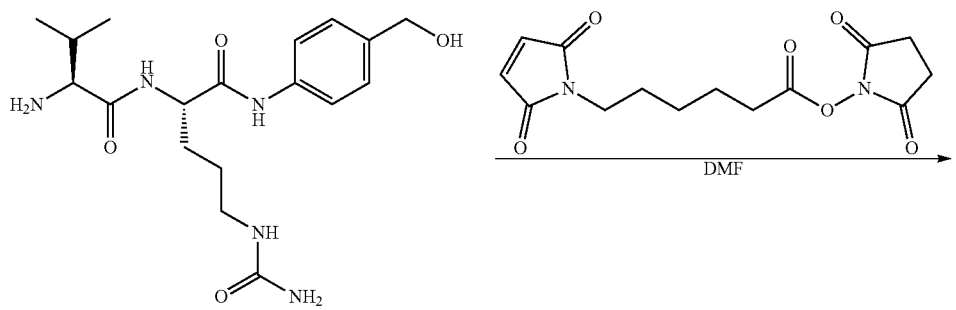
Val-Cit-PABOH
DMF
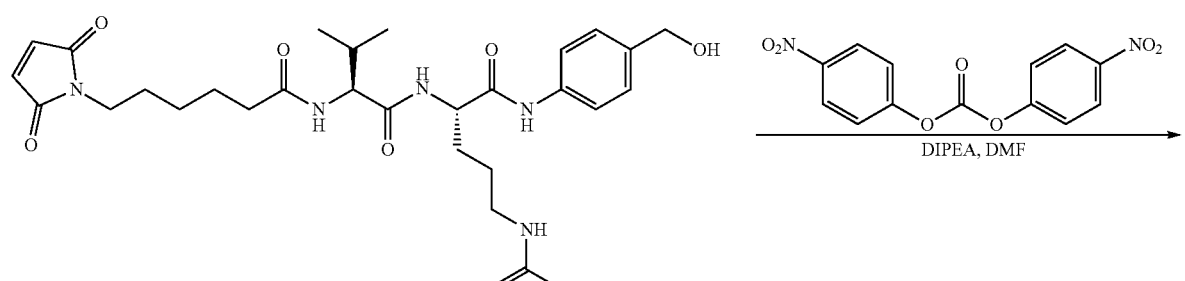
mc-Val-Cit-PABOH
DIPEA, DMF

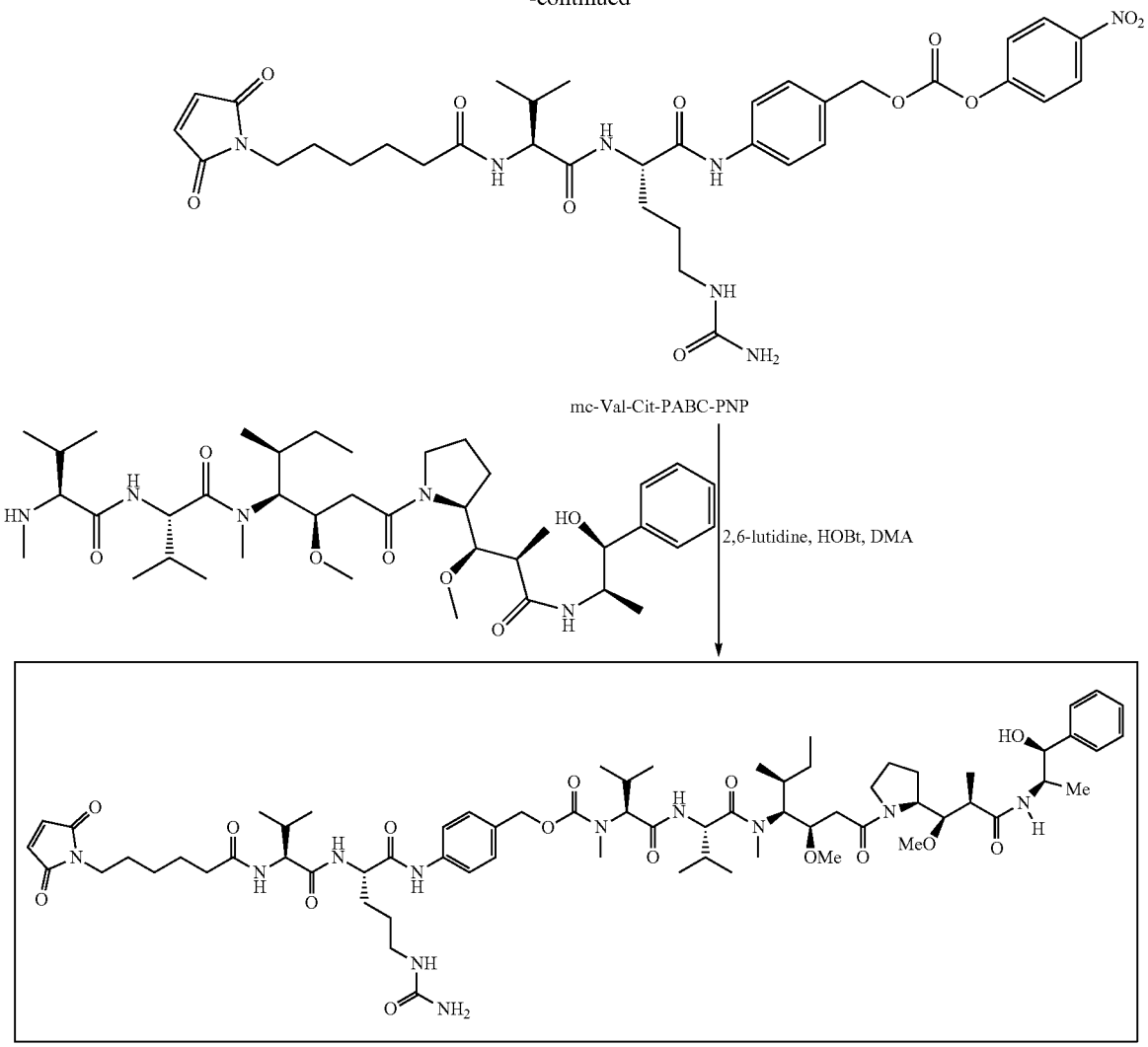

mc-Val-Cit-PABC-PNP 2,6-lutidine, HOBt, DMA

EXAMPLES

Example 1. Synthesis of Fmoc-Val-OSu

Fmoc-Val-OSu is commercially available or can be prepared following the procedure below.

Fmoc-Val-OH (1.0 eq.), N-hydroxysuccinimide (1.3 eq.) were dissolved in a mixture of DCM (6 vol.) and THE (2 vol.). Separately, EDC.HCl (1.2 eq.) was solubilized in DCM (10 vol.) and the solution was cooled to 0-5° C. The Fmoc-Val-OSu/NHS solution was then added to the EDC solution before warming up the reaction mixture to 20-25° C. The reaction mixture was stirred at 20-25° C. until reaction was complete. The reaction mixture was then concentrated under reduced pressure at 40-60° C. and azeotropically distilled twice with THF. The concentrated residue was dissolved with THE and filtered to remove EDU. The filtrate was concentrated under reduced pressure at 40-60° C. and re-slurried with n-heptane at 5-10° C. for 12 hours. Solids were filtered, washed and dried under vacuum (96% yield). MS: m/e 437 (MH)+, 459 (M+Na)+.

Example 2. Synthesis of Fmoc-Val-Cit

Fmoc-Val-OSu (1 eq.) was dissolved in Acetonitrile (5 vol.) at 20° C. Separately, sodium carbonate (1.1 eq.) was solubilized in Water (5 vol.) at 20° C. and L-Citrulline (1.1 eq.) was then added to give a homogeneous clear solution. Water (0.5 vol.) was added to the Fmoc-Val-OSu solution and the reaction mixture was heated to 35° C. before adding the prepared citrulline solution dropwise over 10 min. The reaction mixture was stirred at 35° C. for 3-4 hours until reaction was complete before being cooled to 20° C. Acetonitrile (20 vol.) was then added over 2-3 hours at 20° C. The resulting suspension was stirred for 1-3 hours before being cooled to 0-5° C. over 1-4 hours and stirred at that temperature for 2-3 hours. Solids were filtered, washed and dried under vacuum before being re-dissolved in a mixture of N,N-dimethylformamide (3.9 vol.), 35.9 g/L aqueous NaCl solution (3.9 vol.), 10% isopropanol in Ethyl acetate (19.5 vol.) at 20° C. Glacial acetic acid (1.3 vol.) was then added and the pH of the solution was adjusted to <2 with concentrated hydrochloric acid (0.78 vol.). After stirring at 20° C. for 30 minutes, phases were separated and the aqueous layer was re-extracted with Ethyl acetate (6.5 vol.). Combined organic layers were washed three times with a mixture of 179.5 g/L aqueous NaCl solution (6.5 vol.) and anhydrous N,N-Dimethylformamide (0.72 vol.). The resulting organic mixture was concentrated to a white paste and diluted with Methanol (19.5 vol.). The resulting suspension is stirred at 20° C. for 10-14 hours before being concentrated again to a white paste. Methyl tert-butyl ether (19.5 vol.) was then added and the resulting suspension was stirred at 40° C. for 1-2 hours. After cooling to 20° C. and stirring followed by cooling to 0-5° C. and stirring, solids were filtered, washed and dried under vacuum. Solids were re-slurried twice in a mixture of Methanol (1.3 vol.) and Methyl tert-butyl ether (19.5 vol.) and dried under vacuum (74% yield). MS: m/e 497 (MH)+, 519 (M+Na)+.

Example 3. Synthesis of Fmoc-Val-Cit-PABOH

Fmoc-Val-Cit (1 eq.), HATU (1.4 eq.) were solubilized in a mixture of anhydrous N,N-Dimethylformamide (9.5 vol.) and Ethyl acetate (5 vol.) at 20° C. The reaction mixture was then cooled to 0-5° C. Separately, a solution of 4-Aminobenzyl alcohol (1.5 eq.) in Ethyl acetate (2 vol.) and anhydrous N,N-Dimethylformamide (0.5 vol.) was prepared. A solution of N,N-Diisopropylethylamine (1.4 eq.) in Ethyl acetate (2 vol.) was also prepared. Water (1 vol.) was added to the cooled Fmoc-Val-Cit/HATU solution before adding the 4-Aminobenzyl alcohol solution quickly. Immediately thereafter, the DIPEA solution was added over 25-35 minutes. The reaction mixture was stirred at 0-5° C. for 1-2 hours until reaction was complete. Pre-chilled Methyl tert-butyl ether (20 vol.) was then added over 10 minutes and the resulting mixture was stirred for 1-3 hours. Solids were filtered, washed and dried under vacuum. Solids were re-slurried in Acetonitrile (20 vol.), filtered, washed and dried under vacuum (80% yield). MS: m/e 602 (MH)+, 624 (M+Na)+.

Example 4. Synthesis of Val-Cit-PABOH

Fmoc-Val-Cit-PABOH (1 eq.) was suspended in anhydrous N,N-Dimethylformamide (5 vol.) and the resulting suspension was stirred at 20° C. until a homogeneous suspension formed. Diethylamine (2 eq.) was then added at 20° C. and the reaction mixture was stirred at 20° C. for 2-3 hours until reaction was complete. Acetonitrile (2 vol.) was then added and distilled off three times to remove the base. The reaction mixture was heated to 35° C. and Ethyl acetate (5 vol.) was added over 60 minutes at 35° C. Methyl tert-butyl ether (10 vol.) was then added over 60 minutes at 35° C. The resulting mixture was stirred at 40° C. for 2-4 hours until a homogeneous suspension was obtained and then cooled to 20° C. over 90 minutes. The suspension was then stirred at 20° C. for 1 hour before being cooled to 0-5° C. over 90 minutes. The product suspension was stirred at 0-5° C. for 2-3 hours before being filtered, washed and dried under vacuum. Solids were re-suspended in Methyl tert-butyl ether (15 vol.) and the resulting mixture was heated to 40° C. and stirred at that temperature for 1-2 hours until a homogeneous suspension was obtained. The resulting mixture was cooled to 20° C. and stirred at that temperature for 2-4 hours before being filtered, washed and dried under vacuum (90% yield). MS: m/e 380 (M)+, 402 (M+Na)+.

Example 5. Synthesis of mc-Val-Cit-PABOH

To me-OSu (1.7 eq.) was added anhydrous N,N-Dimethylformamide (3 vol.) and the resulting mixture was stirred at 20° C. until a clear colorless solution formed. A solution of Val-Cit-PABOH (1 eq.) in anhydrous N,N-Dimethylformamide (7 vol.) was then added over 30 minutes while keeping temperature below 30° C. The reaction mixture was stirred at 30° C. for 5-6 hours until reaction was complete. Ethyl acetate (30 vol.) was then added over 30 minutes at 30° C. The resulting suspension was stirred at that temperature for 10-20 minutes before being cooled to 20° C. and stirred at 20° C. for 2-4 hours. Filtered solids were solubilized in N,N-Dimethylformamide (10 vol.) and the resulting mixture was stirred at 30° C. for 30-60 minutes. Ethyl acetate (30 vol.) was added over 30 minutes at 30° C. The resulting suspension was stirred at that temperature for 10-20 minutes before being cooled to 20° C. and stirred at 20° C. for 2-4 hours. The resulting solids were collected by filtration, washed and dried under vacuum (97% yield). MS: m/e 573 (M)+, 595 (M+Na)+.

Example 6. Synthesis of mc-Val-Cit-PABC-PNP mc-Val-Cit-PABOH (1 eq.) was mixed with bis(4-nitrophenyl) carbonate (1.87 eq.) in N,N-dimethylformamide (8 vol.) at 20° C. N,N-diisopropylethylamine (1.75 eq.) was added at 25° C. The reaction mixture was stirred at 25° C. for 2-6 hours until reaction was complete. Product was precipitated out of the reaction mixture by adding anhydrous ethyl acetate (12.5 vol.) at 25° C. and tert-Butyl methyl ether (12.5 vol.). The resulting slurry was stirred, then cooled to 0° C. and stirred for 10-30 minutes. The solids were isolated by filtration, washed and dried under vacuum before being re-slurried in ethyl acetate (12.5 vol.) at 20° C., filtered and dried once more (95% yield). MS: m/e 738 (MH)+, 760 (M+Na)+.

Example 7. Synthesis of the Compound of Formula (3)

A compound of the following formula (1 eq.):

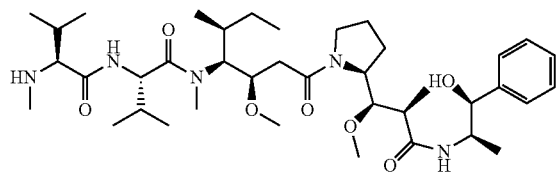 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

and mc-Val-Cit-PABC-PNP (1.18 eq.) were solubilized in N,N-dimethylacetamide (7.87 vol.). 1-Hydroxybenzotriazole (HOBt) hydrate (8.95 wt %) and 2,6-lutidine (2.315 vol.) were then added and the reaction mixture was stirred at 40° C. for 12-16 hours until reaction was complete. The reaction mixture was cooled to 20° C. and added into tert-Butyl methyl ether (168 vol.). The resultant slurry was stirred for 3-5 hours and filtered, washed and dried under vacuum. Crude product was purified by column purification and product-containing fractions were concentrated to dryness and slurried in Ethyl acetate (20 vol.) before being isolated by filtration, washed and dried (65% yield). MS: m/e 1317 (MH)+, 1339 (M+Na)+.

Example 9. Impurity Levels in Mc-Val-Cit-PABOH Synthesized Using Different Reaction Conditions mc-Val-Cit-PABOH was synthesized via the preparation of Fmoc-Val-Cit-PABOH with the various sets of reaction conditions shown in Table 1. An HPLC assay was used to determine the amount of the Formula (4) precursor compound. Area percentages of the Formula (4) precursor compound relative to the mc-Val-Cit-PABOH for each set of reaction conditions are provided in Table 1. As indicated in Table 1 and also as shown in The FIGURE, mc-Val-Cit-PABOH synthesized according to the method described in Example 3 did not contain any detectable amount of Formula (4) precursor compound.

TABLE 1

| Preparation of Fmoc-Val-Cit-PABOH Reaction condition | Impurity area % in mc-Val-Cit-PABOH |
|---|---|
| EEDQ (2 eq), PABOH (2 eq) DCM/MeOH (2:1) | N.T. |
| EEDQ (2 eq), PABOH (2 eq) DCM/MeOH (2:1) | 0.34% |
| EEDQ (2 eq), PABOH (2 eq) THF/MeOH (7:4) | 0.47% 0.14% 0.28% |
| EEDQ (2 eq), PABOH (2 eq) THF/MeOH (2:1) | 0.15% 0.17% |
| EEDQ (1.5 eq), PABOH (1.5 eq) THF/MeOH (2:1) | 0.18% 0.23% 0.25% |
| HATU (1.4 eq), PABOH (1.5 eq) DIPEA (1.4 eq) DMF/EtOAc (1:1) | N.D. |

N.T. = not tested
N.D. = not detectable

Example 10. Optimization of the Reaction Conditions for Formation of Fmoc-Val-Cit-PABOH Different peptide coupling reagents were screened and assessed with respect to diastereomer formation and formation rate of Fmoc-Val-Cit-PABOH. The results are summarized in Table 2.

TABLE 2

| Peptide coupling reagent | Fmoc-Val-Cit area % | Fmoc-Val-Cit-PABOH area % | Diastereomer area % |
|---|---|---|---|
| EEDQ (baseline) | 2.88 | 58.6 | 6.91 |
| T3P | 64.3 | 29.2 | 6.4 |
| CDI | 24.38 | N.D. | N.D. |
| TBTU/HOAt | 1.9 | 73.7 | 4.5 |
| PyBOP/HOAt | 5.2 | 54.2 | 3.9 |
| HATU | 0.15 | 77.9 | 1.4 |
| PyAOP | 7.9 | 69.7 | 11.4 |
| COMU | 3.4 | 75.6 | 3.0 |
| TBTU | 3.8 | 36.0 | 33.2 |
| PyBOP | 3.5 | 38.2 | 42.0 |
| HBTU | 7.7 | 26.9 | 28.6 |

N.D. = not detectable

Reaction conditions using HATU were further optimized by screening different bases for deprotonation of Fmoc-Val-Cit. Weak bases such as 2,6-Lutidine (pKa conjugate acid is 6.6) led to slower reaction rates and increased amounts of impurity whereas strong base DIPEA (pKa conjugate acid is 11.0) showed the best results with limited formation of diastereomer and precursor to the compound of Formula (4).

Different mixtures of N,N-Dimethylformamide (DMF) with other organic solvents were screened as reaction solvent. The use of DMF achieved good solubility of the starting material for the reaction to proceed smoothly. Using ethyl acetate as a co-solvent in a (1:1) mixture with DMF appeared to be the best solvent system to keep fast reaction rate and limited epimerization, as well as facilitating initial isolation of product Fmoc-Val-Cit-PABOH that precipitated out of solution.

Different reaction temperatures were screened. A reaction temperature of 0° C. decreased impurity formation without preventing the reaction from proceeding quickly.

Orders and timings of addition of reagents were screened. Specifically, upon addition of p-aminobenzyl alcohol to a solution of Fmoc-Val-Cit and HATU, initiation of Fmoc-Val-Cit-PABOH formation was observed, asp-aminobenzyl alcohol could act also as a weak base (pKa conjugate acid estimated 4.6-5.1) in the deprotonation of Fmoc-Val-Cit. Addition of the strong base DIPEA right after p-aminobenzyl alcohol charge was observed to prevent the formation of the precursor to the compound of Formula (4) that tends to form in the presence of a weak base.

By reslurrying the initially isolated product in acetonitrile to remove by-products and excess reagents generated during the reaction, Fmoc-Val-Cit-PABOH was further purified.

Different bases were screened with HATU as the coupling reagent and results are presented below in Table 3.

TABLE 3

| Base | Conversion | Ratio Fmoc-Val-Cit-PABOH/diastereomer |
|---|---|---|
| DIPEA | 100% | 13:1 |
| Pyridine | 93% | 49:1 |
| 2,6-lutidine | 93% | 65:1 |

Different solvent systems were screened with HATU as the coupling reagent and results are presented below in Table 4.

TABLE 4

| Solvent | Fmoc-Val-Cit-PABOH area % | Diastereomer area % | Fmoc-Val-Cit area % |
|---|---|---|---|
| DMF:THF (1:1) | 75.8 | 1.7 | 1.1 |
| DMF:EtOAc (1:1) | 77.9 | 1.7 | 1.3 |
| DMF | 79.5 | 3.8 | 1.3 |

Example 11. Isolation and Characterization of the Compound of Formula (4)

Compound (4) was isolated by reverse phase preparative chromatography of impure compound (5) containing low levels of compound (4), using a gradient of 0.05% acetic acid in water and 0.05% acetic acid in acetonitrile/methanol (65:35). Appropriate fractions were pooled based on LCMS analysis. Approximately 400 mg of impure compound (5) was purified in 4 runs to yield 15 mg of compound (4). MS: m/e 1976 (MH)+.

While the foregoing written description of the methods, compounds, and compositions described herein enables one of ordinary skill to make and use the methods, compounds, and compositions described herein, those of ordinary skill will understand and appreciate the existence of variations, combinations, and equivalents of the specific embodiment, method, and examples herein. The methods, compounds, and compositions provided herein should therefore not be limited by the above-described embodiments, methods, or examples, but rather encompasses all embodiments and methods within the scope and spirit of the methods, compounds, and compositions provided herein.

All references disclosed herein are incorporated by reference in their entireties.

The invention claimed is:

1. A method of preparing a compound of Formula (1A):

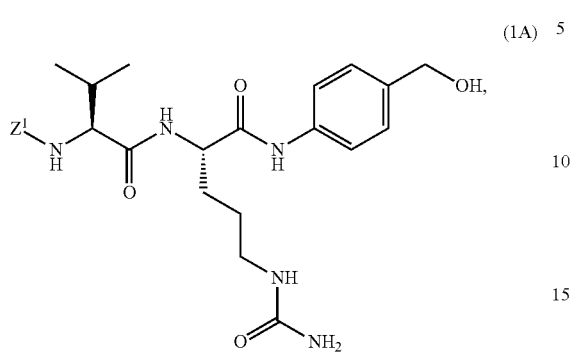
(1A)

or a salt thereof,
wherein $Z^1$ is a protecting group;
the method comprising reacting a compound of Formula (1B) or a salt thereof:

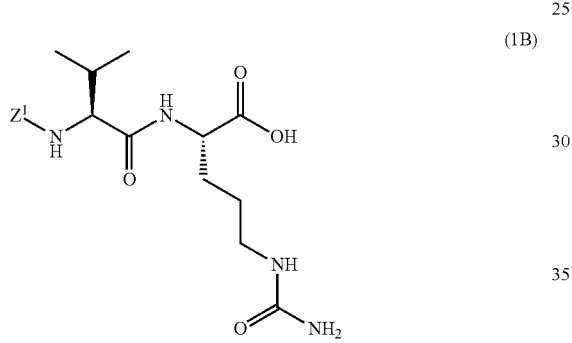
(1B)

with p-aminobenzyl alcohol (PABOH) in the presence of a peptide coupling reagent, wherein
the peptide coupling reagent comprises

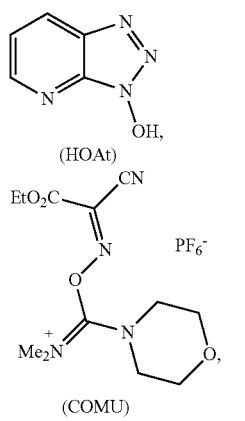

or an HOAt derivative.

2. The method of claim 1, wherein $Z^1$ is an alkoxycarbonyl or aryloxy-carbonyl group.

3. The method of claim 1, wherein $Z^1$ is fluorenylmethyloxycarbonyl (Fmoc).

4. The method of claim 1, wherein the peptide coupling reagent comprises a compound selected from the group consisting of HOAt,

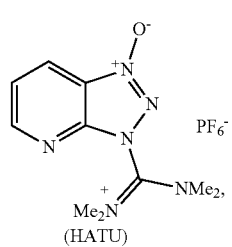
(HATU)

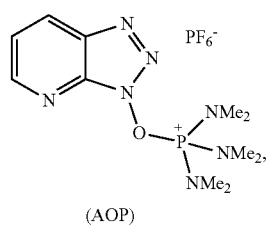
(AOP)

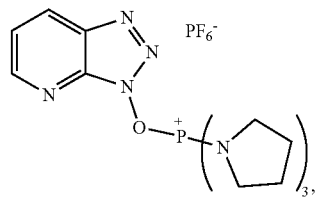
(PyAOP)

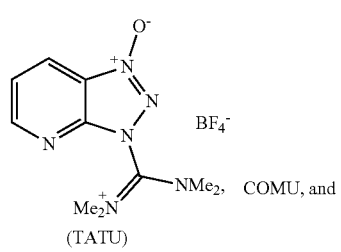
(TATU) COMU, and

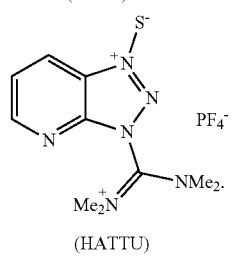
(HATTU)

5. The method of claim 1, wherein the peptide coupling reagent comprises a compound selected from the group consisting of HOAt, HATU, COMU, and PyAOP.

6. The method of claim 5, wherein the peptide coupling reagent further comprises

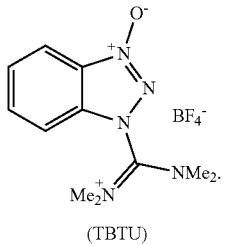

(TBTU)

7. The method of claim 5, wherein the peptide coupling reagent further comprises

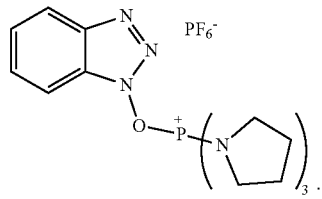

(PyBOP)

8. The method of claim 1, wherein the reaction of the compound of Formula (1B) or a salt thereof with the PABOH is performed in the presence of a base.

9. The method of claim 8, wherein the base is N,N-Diisopropylethylamine (DIPEA).

10. The method of claim 1, wherein the reaction of the compound of Formula (1B) or a salt thereof with the PABOH is performed in an organic solvent.

11. The method of claim 10, wherein the organic solvent comprises N,N-Dimethylformamide (DMF).

12. The method of claim 11, wherein the organic solvent further comprises ethyl acetate.

13. The method of claim 12, wherein the volume ratio of the DMF to the ethyl acetate is about 1:1.

14. The method of claim 1, wherein the reaction of the compound of Formula (1B) or a salt thereof with the PAB OH is performed at a temperature of no more than about 5° C.

15. The method of claim 9, wherein the PABOH is mixed with the compound of Formula (1B) or a salt thereof before addition of the DIPEA.

16. The method of claim 15, wherein the DIPEA is added within 5 minutes after the PABOH is mixed with the compound of Formula (1B) or a salt thereof.

17. The method of claim 1, wherein the compound of formula (1B) or a salt thereof is obtained by reacting a compound of Formula (1C) or a salt thereof,

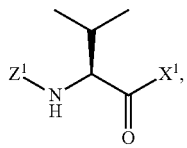

(1C)

wherein $X^1$ is a carboxyl-activating group, with

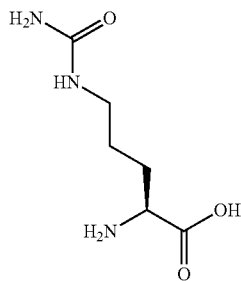 [SMILES: NC(=O)NCCC[C@H](N)C(=O)O]

or a salt thereof to form the compound of Formula (1B) or salt thereof.

18. The method of claim 17, wherein $X^1$ is

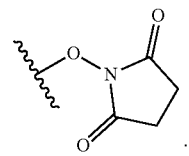 [SMILES: *ON1C(=O)CCC1=O]

19. The method of claim 1, further comprising converting the compound of Formula (1A) or a salt thereof to a compound of Formula (1D) or a salt thereof:

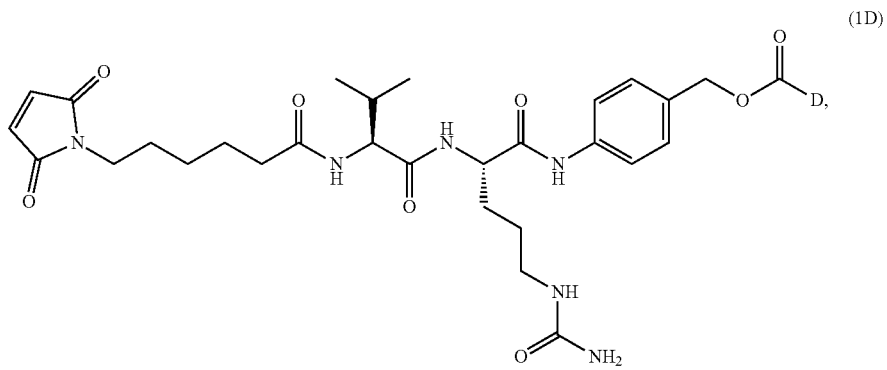

(1D)

wherein D is a moiety of Formula (D):

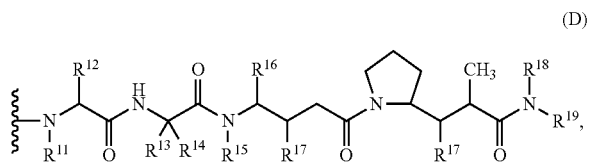

(D)

wherein the wavy line indicates covalent bonding of D to the remainder of the compound;
$R^{11}$ is selected from the group consisting of H and C1-C8 alkyl;
$R^{12}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);
$R^{13}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);
$R^{14}$ is selected from the group consisting of H and methyl;
or $R^{13}$ and $R^{14}$ jointly form a carbocyclic ring and have the formula —$(CR^aR^b)_n$—, wherein $R^a$ and $R^b$ are independently selected from the group consisting of H, $C_1$-$C_8$ alkyl and $C_3$-$C_8$ carbocyclyl, and n is selected from the group consisting of 2, 3, 4, 5 and 6;
$R^{15}$ is selected from the group consisting of H and $C_1$-$C_8$ alkyl;
$R^{16}$ is selected from the group consisting of H, $C_1$-$C_8$ alkyl, $C_3$-$C_8$ carbocyclyl, aryl, $C_1$-$C_8$ alkyl-aryl, $C_1$-$C_8$ alkyl-($C_3$-$C_8$ carbocyclyl), $C_3$-$C_8$ heterocyclyl, and $C_1$-$C_8$ alkyl-($C_3$-$C_8$ heterocyclyl);
each $R^{17}$ is independently selected from the group consisting of H, OH, $C_1$-$C_8$ alkyl, $C_3$-$C_8$ carbocyclyl, and —O—($C_1$-$C_8$ alkyl);
$R^{18}$ is selected from the group consisting of H and $C_1$-$C_8$ alkyl;
$R^{19}$ is selected from the group consisting of —C($R^{17}$)$_2$—C($R^{17}$)$_2$-aryl, —C($R^{17}$)$_2$—C($R^{17}$)$_2$—($C_3$-$C_8$ heterocyclyl), —C($R^{17}$)$_2$—C(O)—Z$R^{20}$, and —C($R^{17}$)$_2$—C($R^{17}$)$_2$—($C_3$-$C_8$ carbocyclyl);
$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl; and
Z is —O—, or —NH—, or Z— is —O— and $R^{20}$ is $C_1$-$C_4$ alkyl or Z is —NH— and $R^{20}$ is optionally substituted phenyl or optionally substituted $C_5$-$C_6$ heteroaryl.

20. The method of claim 19, wherein the conversion of the compound of Formula (1A) or a salt thereof to the compound of Formula (1D) or a salt thereof comprises converting the compound of Formula (1A) or a salt thereof to a compound of Formula (1E) or a salt thereof:

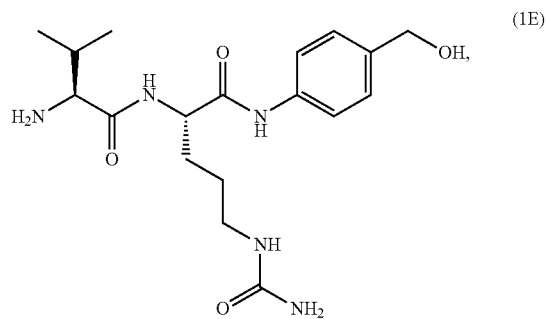 [SMILES: CC(C)[C@H](N)C(=O)N[C@@H](CCCNC(N)=O)C(=O)Nc1ccc(CO)cc1]

(1E)

and converting the compound of Formula (1E) or a salt thereof to the compound of Formula (1D) or a salt thereof.

21. The method of claim 20, wherein the conversion of the compound of Formula (1A) or a salt thereof to the compound of Formula (1D) or a salt thereof further comprises reacting the compound of Formula (1E) or a salt thereof with a compound of Formula (1F):

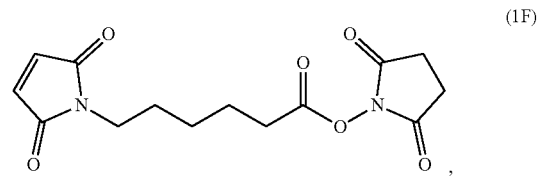 [SMILES: O=C(CCCCCN1C(=O)C=CC1=O)ON1C(=O)CCC1=O]

(1F)

to form a compound of Formula (1G) or a salt thereof:

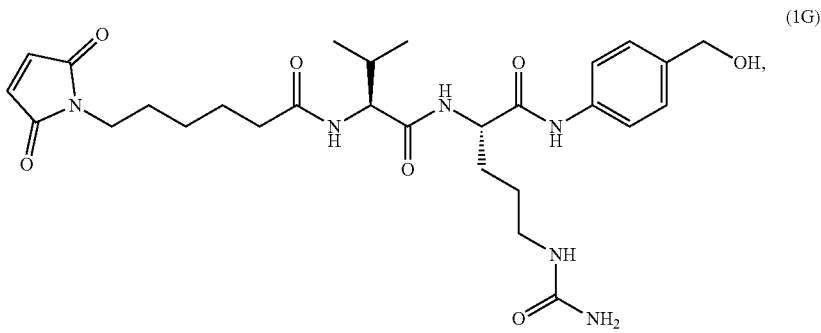 [SMILES: CC(C)[C@H](NC(=O)CCCCCN1C(=O)C=CC1=O)C(=O)N[C@@H](CCCNC(N)=O)C(=O)Nc1ccc(CO)cc1]

(1G)

and converting the compound of Formula (1G) or a salt thereof to the compound of Formula (1D) or a salt thereof.

22. The method of claim 21, wherein the conversion of the compound of Formula (1A) or a salt thereof to the compound of Formula (1D) or a salt thereof further comprises reacting the compound of Formula (1G) or a salt thereof with a compound of Formula (1H):

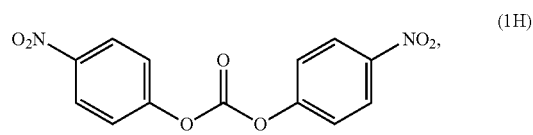 [SMILES: O=C(Oc1ccc([N+](=O)[O-])cc1)Oc1ccc([N+](=O)[O-])cc1]

to form a compound of Formula (1I) or a salt thereof:

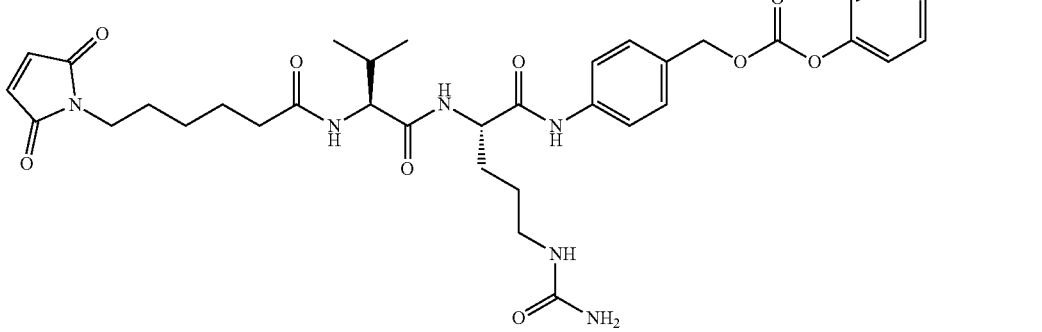

and converting the compound of Formula (1I) or a salt thereof to the compound of Formula (1D) or a salt thereof.

23. The method of claim 22, wherein the conversion of the compound of Formula (1A) or a salt thereof to the compound of Formula (1D) or a salt thereof further comprises reacting the compound of Formula (1I) or a salt thereof with a compound of Formula (1J) or a salt thereof:

(1J)

to form the compound of Formula (1D) or a salt thereof.

24. The method of claim 1, further comprising converting the compound of Formula (1A) or a salt thereof to a compound of Formula (1D) or a salt thereof:

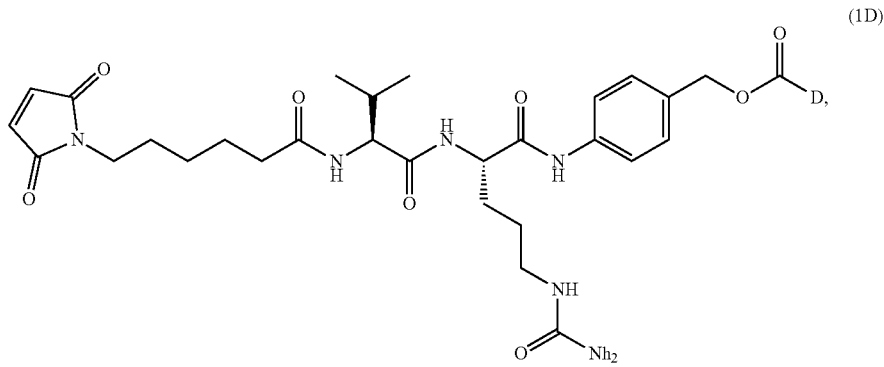

wherein D of Formula (1D) is a moiety of any one of Formulae $D_{E-1}$, $D_{E-2}$, $D_{F-1}$ and $D_{F/E-3}$:

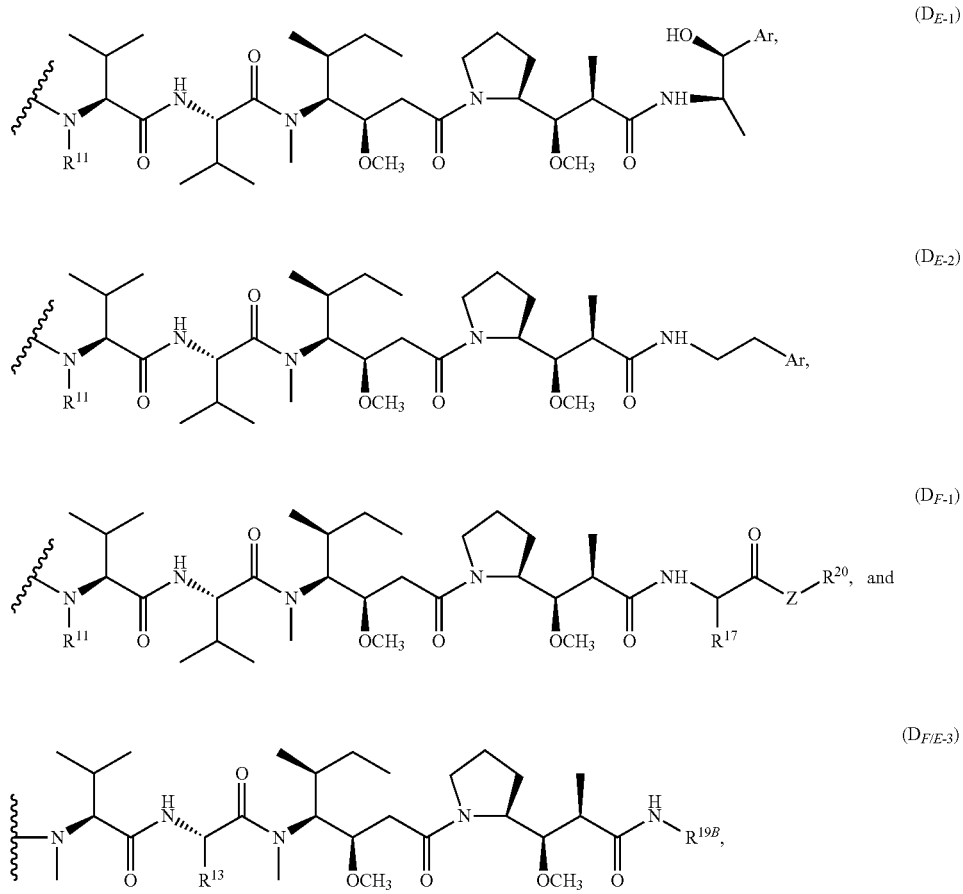

wherein the wavy line indicates covalent bonding of D to the remainder of the compound;

$R^{11}$ is selected from the group consisting of H and $C_1$-$C_8$ alkyl;

$R^{13}$ is isopropyl or —$CH_2$—$CH(CH_3)_2$;

$R^{17}$ is selected from the group consisting of H, OH, $C_1$-$C_8$ alkyl, $C_3$-$C_8$ carbocyclyl, and —O—($C_1$-$C_8$ alkyl);

$R^{19B}$ of Formula $D_{F/E-3}$ is —CH($CH_3$)—CH(OH)Ph, —CH($CO_2$H)$CH_2$Ph, —CH($CH_2$Ph)-2-thiazole, —CH($CH_2$Ph)-2-pyridyl, —CH($CH_2$)-p-Cl-Ph, —CH($CO_2$Me)-$CH_2$Ph, —CH($CO_2$Me)-$CH_2CH_2SCH_3$, CH($CH_2CH_2SCH_3$)C(=O)NH-3-quinolyl, or —CH($CH_2$Ph)C(=O)NH-p-Cl-Ph;

$R^{20}$ is selected from the group consisting of H, $C_1$-$C_8$ alkyl, optionally substituted $C_6$-$C_{10}$ aryl, optionally substituted $C_5$-$C_{10}$ heteroaryl and $C_3$-$C_8$ heterocyclyl; and Ar is optionally substituted $C_6$-$C_{10}$ aryl or optionally substituted $C_3$-$C_8$ heterocyclyl.

25. The method of claim 19, wherein D is a moiety of Formula (D1):

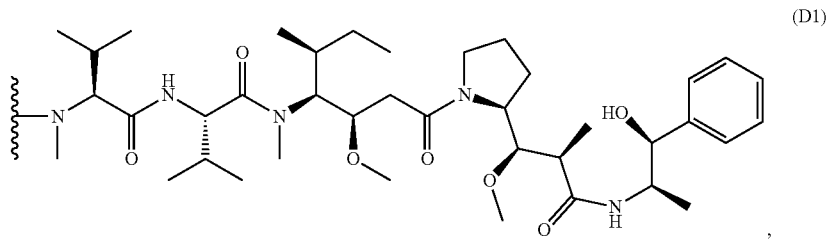 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

wherein the wavy line indicates covalent bonding of D to the remainder of the compound.

26. A compound of Formula (4):
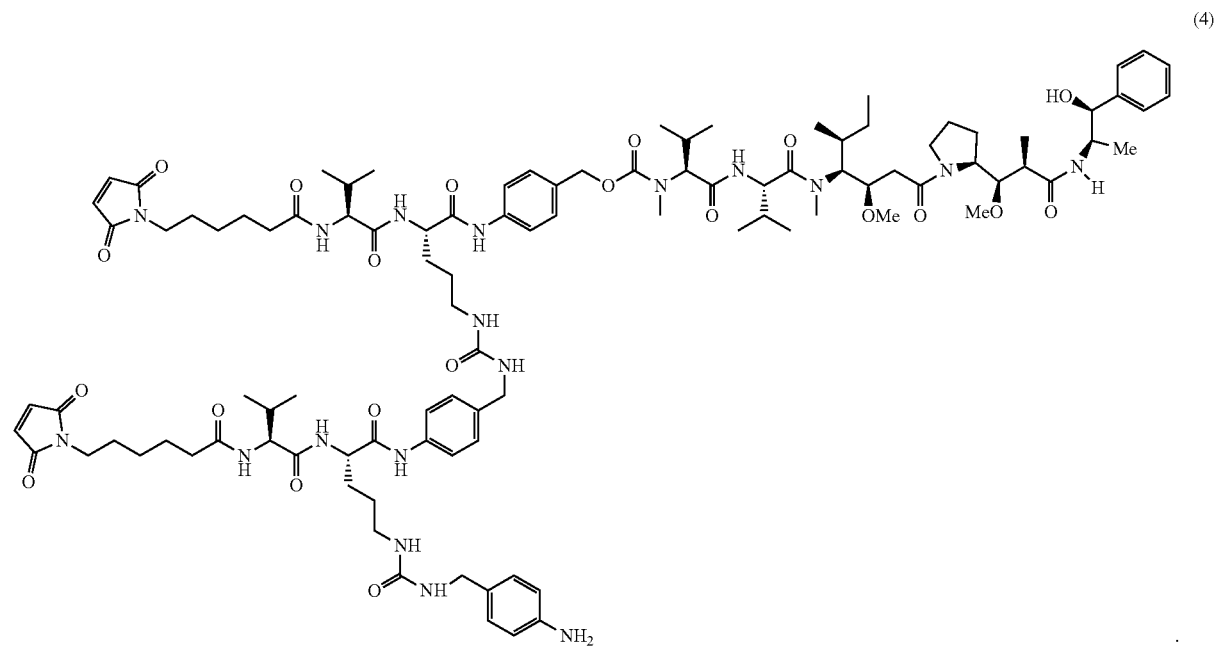 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(=O)NCc2ccc(NC(=O)[C@H](CCCNC(=O)NCc3ccc(N)cc3)NC(=O)[C@@H](NC(=O)CCCCCN3C(=O)C=CC3=O)C(C)C)cc2)NC(=O)[C@@H](NC(=O)CCCCCN2C(=O)C=CC2=O)C(C)C)cc1)C(C)C]
(4)
27. The compound of claim 26, wherein the compound is isolated.
28. A composition comprising a compound of Formula (3),
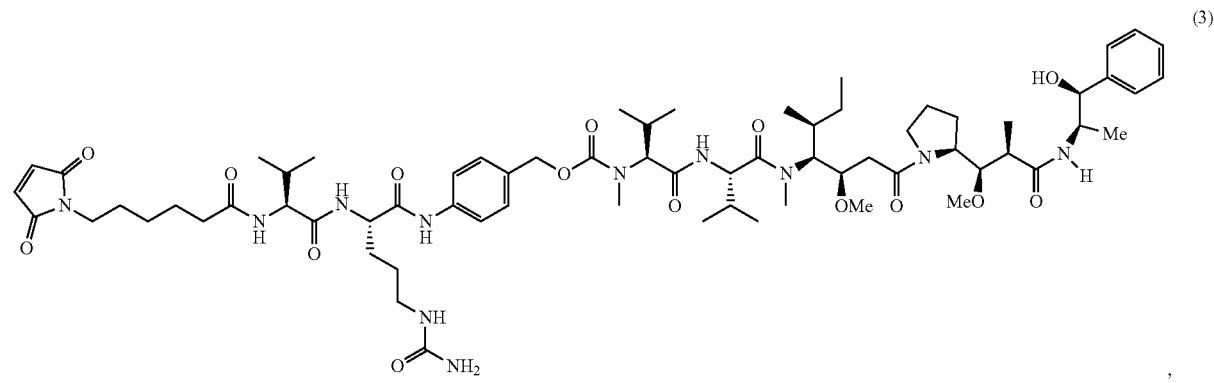 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]
(3)

and a compound of Formula (4):

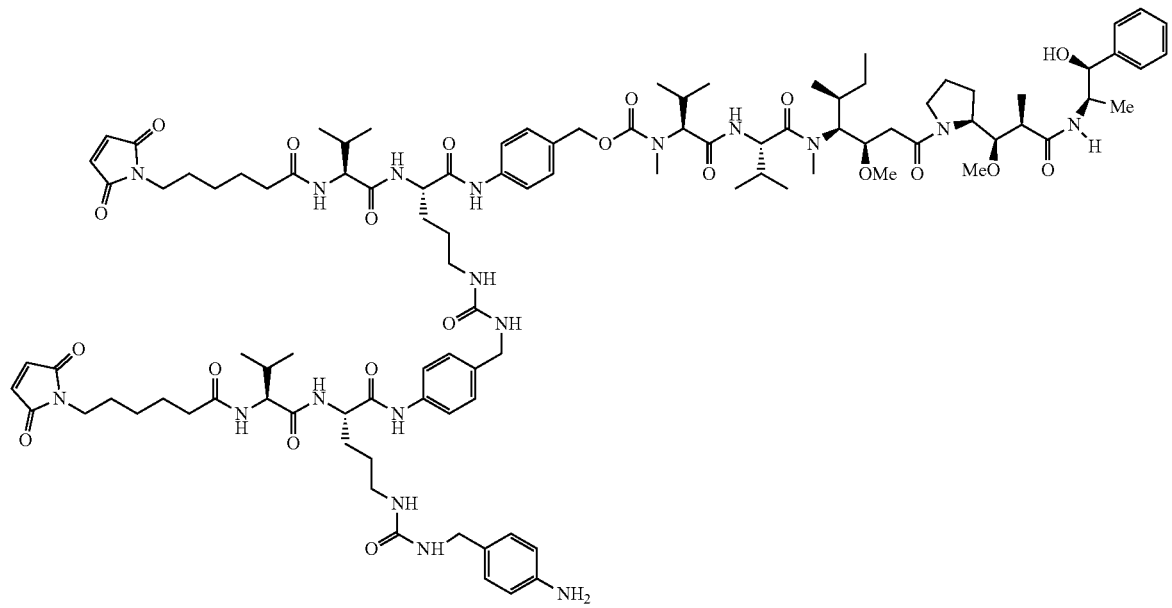

(4)

wherein the molar ratio of the compound of Formula (4) to the compound of Formula (3) is no more than 0.1%.

29. The composition of claim 28, further comprising a pharmaceutically acceptable carrier or excipient.

30. The composition of claim 28, wherein the molar ratio of the compound of Formula (4) to the compound of Formula (3) is no more than about 0.05%.

31. The composition of claim 28, wherein the molar ratio of the compound of Formula (4) to the compound of Formula (3) is no more than about 0.01%.

32. The composition of claim 28, wherein the molar ratio of the compound of Formula (4) to the compound of Formula (3) is no more than about 0.005%.

33. The composition of claim 28, wherein the molar ratio of the compound of Formula (4) to the compound of Formula (3) is no more than about 0.001%.

34. The composition of claim 28, wherein the molar ratio of the compound of Formula (4) to the compound of Formula (3) is no more than about 0.0005%.

35. The composition of claim 28, wherein the molar ratio of the compound of Formula (4) to the compound of Formula (3) is no more than about 0.0001%.

* * * * *

UNITED STATES PATENT AND TRADEMARK OFFICE
CERTIFICATE OF CORRECTION

Page 1 of 2

PATENT NO. : 11,612,666 B2
APPLICATION NO. : 16/768027
DATED : March 28, 2023
INVENTOR(S) : Sophie Blanchard et al.

It is certified that error appears in the above-identified patent and that said Letters Patent is hereby corrected as shown below:

On the Title Page

Item (56) under OTHER PUBLICATIONS:

At Column 2, Line number 13:
Please replace "Report Report"
With --Report--;

At Column 2, Line number 29:
Please replace "Antineopiastic"
With --"Antineoplastic--;

At Column 2, Line number 30:
Please replace "Conjgates""
With --Conjugates,"--.

In the Claims

At Column 60, Claim number 4, Line numbers 54-63 (Approx.):

Please replace " 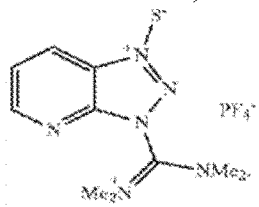 "

Signed and Sealed this
Seventeenth Day of October, 2023

Katherine Kelly Vidal
Director of the United States Patent and Trademark Office

CERTIFICATE OF CORRECTION (continued)
U.S. Pat. No. 11,612,666 B2

With -- 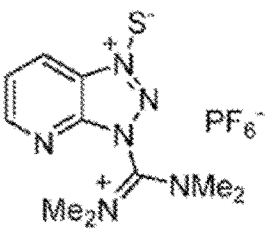 (HATTU)--;

At Column 62, Claim number 17, Line number 35:
Please insert --a-- before "salt";

At Column 63, Claim number 19, Line 15 (Approx.):
Please replace "C1-C8"
With --$C_1$-$C_8$--;

At Column 64, Claim number 19, Line 1:
Please replace "Z—is"
With --Z is--.